(12) United States Patent
Gielen-Haertwig et al.

(10) Patent No.: US 7,687,510 B2
(45) Date of Patent: Mar. 30, 2010

(54) PYRIMIDINONE DERIVATIVES AS THERAPEUTIC AGENTS AGAINST ACUTE AND CHRONIC INFLAMMATORY, ISCHAEMIC AND REMODELLING PROCESSES

(75) Inventors: Heike Gielen-Haertwig, Monheim (DE); Volkhart Min-Jian Li, Velbert (DE); Ulrich Rosentreter, Wuppertal (DE); Karl-Heinz Schlemmer, Wuppertal (DE); Swen Allerheiligen, Essen (DE); Leila Telan, Wuppertal (DE); Lars Bärfacker, Oberhausen (DE); Jörg Keldenich, Wuppertal (DE); Mary F. Fitzgerald, Oxford (GB); Kevin Nash, Herts (GB); Barbara Albrecht, Wülfrath (DE); Dirk Meurer, Pulheim (DE)

(73) Assignee: Bayer Healthcare AG, Leverkusen (DE)

( * ) Notice: Subject to any disclaimer, the term of this patent is extended or adjusted under 35 U.S.C. 154(b) by 1011 days.

(21) Appl. No.: 10/527,391

(22) PCT Filed: Aug. 28, 2003

(86) PCT No.: PCT/EP03/09525

§ 371 (c)(1), (2), (4) Date: Oct. 21, 2005

(87) PCT Pub. No.: WO2004/024700

PCT Pub. Date: Mar. 25, 2004

(65) Prior Publication Data

US 2006/0160801 A1    Jul. 20, 2006

(30) Foreign Application Priority Data

| Sep. 10, 2002 | (GB) | ................................ 0220962.5 |
| Nov. 14, 2002 | (GB) | ................................ 0226609.6 |
| Jul. 7, 2003 | (GB) | ................................ 0315870.6 |

(51) Int. Cl.
*C07D 239/22* (2006.01)
*C07D 401/04* (2006.01)
*A61K 31/5377* (2006.01)

(52) U.S. Cl. ...................................... 514/274; 544/315
(58) Field of Classification Search ................. 544/315; 514/274
See application file for complete search history.

(56) References Cited

U.S. PATENT DOCUMENTS 5,532,366 A    7/1996    Edwards et al. .......... 514/234.2

FOREIGN PATENT DOCUMENTS

| EP | 0528633 | 2/1993 |
| WO | 0137837 | 3/2001 |

OTHER PUBLICATIONS

Namazi et al., Investigation of the chemical reactivity of positions N-3, C-5 and C6-mehtyl group in Biginelli type compounds and synthesis of new dihydropyrimidine derivatives, Journal of Heterocyclic Chemistry, 38(5): 1051-1054, 2001.*
Stockley et al., Neutrophils and Protease/Antiprotease Imbalance, Am J Respir Crit Care Med, 160:S49-S52, 1999.*
Lewandowski, K., et al., "A Combinatorial Approach to Recognition of Chirality: Preparation of Highly Enantioselective Aryl-Dihydropyrimidine Selectors for Chiral HPLC", J. Comb. Chem., 1(1): 105-112 (1999).
Chimicheskaya encyclopedia, Nauchnoe izd-vo "Bolshaya Rossiskaya encyclopedia", Moscow (1995), vol. 4, p. 380, col. 752. English translation attached.

* cited by examiner

*Primary Examiner*—Deepak Rao
(74) *Attorney, Agent, or Firm*—Edwards Angell Palmer & Dodge LLP; Barry Kramer; Ralph A. Loren

(57) ABSTRACT

The invention relates to novel heterocyclic derivatives, processes for their preparation, and their use in medicaments, especially for the treatment of chronic obstructive pulmonary diseases.

23 Claims, No Drawings

PYRIMIDINONE DERIVATIVES AS THERAPEUTIC AGENTS AGAINST ACUTE AND CHRONIC INFLAMMATORY, ISCHAEMIC AND REMODELLING PROCESSES

RELATED APPLICATIONS/PATENTS AND INCORPORATION BY REFERENCE

This application is a National Stage Application filed under 35 U.S.C. §371 based on International Application No. PCT/EP03/09525, filed Aug. 28, 2003, which claims priority to United Kingdom Patent Application Nos. 0220962.5, filed Sep. 10, 2002, 0226609.6, filed Nov. 14, 2002, and 0315870.6, filed Jul. 7, 2003, the entire contents each of which are incorporated herein by reference. The foregoing applications, and all documents cited therein and all documents cited or referenced therein, and all documents cited or referenced herein, including any U.S. or foreign patents or published patent applications, International patent applications, as well as, any non-patent literature references and any manufacturer's instructions, are hereby expressly incorporated herein by reference.

The present invention relates to novel heterocyclic derivatives, processes for their preparation, and their use in medicaments, especially for the treatment of chronic obstructive pulmonary diseases, acute coronary syndrome, acute myocardial infarction and heart failure development.

The fibrous protein elastin, which comprises an appreciable percentage of all protein content in some tissues, such as the arteries, some ligaments, the lungs and the heart, can be hydrolysed or otherwise destroyed by a select group of enzymes classified as elastases. Human leukocyte elastase (HLE, EC 3.4.21.37), also known as human neutrophil elastase (HNE), is a glycosylated, strongly basic serine protease and is found in the azurophilic granules of human polymorphonuclear leukocytes (PMN). HNE is released from activated PMN and has been implicated causally in the pathogenesis of acute and chronic inflammatory diseases. HNE is capable of degrading a wide range of matrix proteins including elastin and collagen, and in addition to these actions on connective tissue HNE has a broad range of inflammatory actions including upregulation of IL-8 gene expression, oedema formation, mucus gland hyperplasia and mucus hypersecretion. It also acts as a mediator of tissue injury by hydrolysing collagen structures, e.g. in the heart after acute myocardial infarction or during the development of heart failure, thus damaging endothelial cells, promoting extravasation of neutrophils adhering to the endothelium and influencing the adhesion process itself.

Pulmonary diseases where HNE is believed to play a role include lung fibrosis, pneumonia, acute respiratory distress syndrome (ARDS), pulmonary emphysema, including smoking-induced emphysema, chronic obstructive pulmonary diseases (COPD) and cystic fibrosis. In cardiovascular diseases, HNE is involved in the enhanced generation of ischaemic tissue injury followed by myocardial dysfunction after acute myocardial infarction and in the remodelling processes occurring during the development of heart failure. HE has also been causally implicated in rheumatoid arthritis, atherosclerosis, brain trauma, cancer and related conditions in which neutrophil participation is involved.

Thus, inhibitors of HLE activity can be potentially useful in the treatment of a number of inflammatory diseases, especially of chronic obstructive pulmonary diseases [R. A. Stockley, *Neutrophils and protease/antiprotease imbalance*, Am. J. Respir. Crit. Care 160, S49-S52 (1999)]. Inhibitors of HLE activity can also be potentially useful in the treatment of acute myocardial syndrome, unstable angina pectoris, acute myocardial infarction and coronary artery bypass grafts (CABG) [C. P. Tiefenbacher et al., *Inhibition of elastase improves myocardial function after repetitive ischaemia and myocardial infarction in the rat heart*, Eur. J. Physiol. 433, S563-S570 (1997); Dinerman et al, *Increased neutrophil elastase release in unstable angina pectoris and acute myocardial infarction*, J. Am. Coll. Cardiol. 15, 1559-1563 (1990)], of the development of heart failure [S. J. Gilbert et al., *Increased expression of promatrix metalloproteinase-9 and neutrophil elastase in canine dilated cardiomyopathy*, Cardiov. Res. 34, S377-S383 (1997)] and of atherosclerosis [Dollery et al., *Neutrophil elastase in human atherosclerotic plaque*, Circulation 107, 2829-2836 (2003)].

The synthesis of 5-ethoxycarbonyl-1-phenyl-6-methyl-4-(3-nitrophenyl)-3,4-dihydropyrimidin-2(1H)-one is described in J. Heterocyclic Chem. 38, 1051 (2001). A pharmacological activity of this compound is not mentioned.

The present invention relates to compounds of the general formula (I)

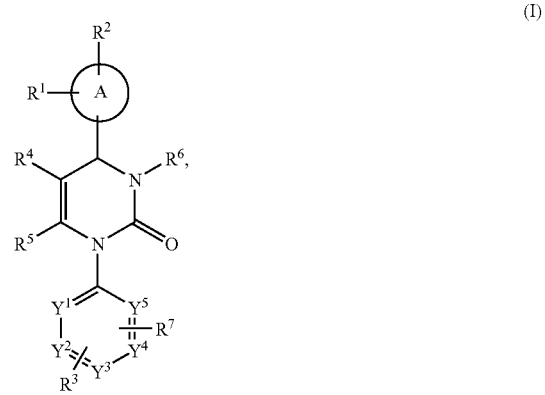

wherein

A represents an aryl or heteroaryl ring, $R^1$, $R^2$ and $R^3$ independently from each other represent hydrogen, halogen, nitro, cyano, $C_1$-$C_6$-alkyl, hydroxy or $C_1$-$C_6$-alkoxy, wherein $C_1$-$C_6$-alkyl and $C_1$-$C_6$-alkoxy can be further substituted with one to three identical or different radicals selected from the group consisting of halogen, hydroxy and $C_1$-$C_4$-alkoxy, $R^4$ represents trifluoromethylcarbonyl, $C_1$-$C_6$-alkylcarbonyl, $C_1$-$C_6$-alkoxy-carbonyl, $C_1$-$C_6$-alkenoxycarbonyl, hydroxycarbonyl, aminocarbonyl, mono- or di-$C_1$-$C_4$-alkylaminocarbonyl, $C_6$-$C_{10}$-arylaminocarbonyl, arylcarbonyl, heteroarylcarbonyl, heterocyclylcarbonyl, heteroaryl, heterocyclyl or cyano, wherein $C_1$-$C_6$-alkylcarbonyl, $C_1$-$C_6$-alkoxycarbonyl, mono- and di-$C_1$-$C_4$-alkylaminocarbonyl can be further substituted with one to three identical or different radicals selected from the group consisting of $C_3$-$C_8$-cycloalkyl, hydroxy, $C_1$-$C_4$-alkoxy, $C_1$-$C_4$-alkoxycarbonyl, hydroxycarbonyl, amino-carbonyl, mono- and di-$C_1$-$C_4$-alkylaminocarbonyl, $C_1$-$C_4$-alkylcarbonyl-amino, ($C_1$-$C_4$-alkylcarbonyl)-$C_1$-$C_4$-alkylamino, cyano, amino, mono- and di-$C_1$-$C_4$-alkylamino, heteroaryl, heterocyclyl and tri-($C_1$-$C_6$-alkyl)-silyl, and wherein heteroarylcarbonyl, heterocyclylcarbonyl, heteroaryl and hetero-cyclyl can be further substituted with $C_1$-$C_4$-alkyl, $R^5$ represents $C_1$-$C_4$-alkyl which can be substituted with one to three identical or different radicals selected from the group consisting of halogen, hydroxy, $C_1$-$C_6$-alkoxy, $C_1$-$C_6$-alkenoxy, $C_1$-$C_6$-alkylthio, amino, mono- and di-$C_1$-$C_6$-alkylamino, arylamino, hydroxycarbonyl, $C_1$-$C_6$-alkoxycarbonyl and the radical —O—$C_1$-$C_4$-alkyl-O—$C_1$-$C_4$-alkyl or $R^5$ represents amino, $R^6$ represents hydrogen, $C_1$-$C_6$-alkyl, formyl, aminocarbonyl, mono- or di-$C_1$-$C_4$-alkylaminocarbonyl, $C_3$-$C_8$-cycloalkylcarbonyl, $C_1$-$C_6$-alkylcarbonyl, $C_1$-$C_6$-alkoxycarbonyl, N—($C_1$-$C_4$-alkylsulfonyl)-aminocarbonyl, N—($C_1$-$C_4$-alkyl-sulfonyl)-N—($C_1$-$C_4$-alkyl)-aminocarbonyl, heteroaryl, heterocyclyl, hetero-arylcarbonyl or heterocyclylcarbonyl, wherein $C_1$-$C_6$-alkyl, mono- and di-$C_1$-$C_4$-alkylaminocarbonyl, $C_1$-$C_6$-alkylcarbonyl, $C_1$-$C_6$-alkoxycarbonyl, heteroaryl and heterocyclyl can be substituted with one to three identical or different radicals selected from the group consisting of aryl, heteroaryl, hydroxy, $C_1$-$C_4$-alkoxy, hydroxycarbonyl, $C_1$-$C_6$-alkoxycarbonyl, ammo-carbonyl, mono- and di-$C_1$-$C_4$-alkylaminocarbonyl, amino, mono- and di-$C_1$-$C_4$-alkylamino, $C_1$-$C_4$-alkylcarbonylamino, tri-($C_1$-$C_6$-alkyl)-silyl, cyano, N-(mono- and di-$C_1$-$C_4$-alkylamino-$C_1$-$C_4$-alkyl)-aminocarbonyl, N—($C_1$-$C_4$-alkoxy-$C_1$-$C_4$-alkyl)-aminocarbonyl and halogen, or $R^6$ represents a moiety of the formula

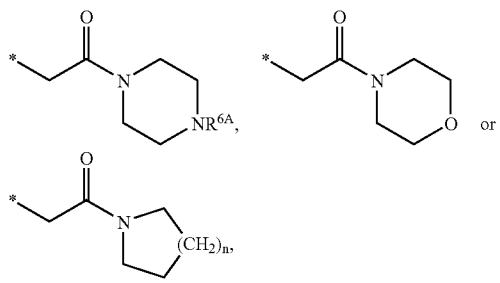

wherein $R^{6A}$ is selected from the group consisting of hydrogen and $C_1$-$C_6$-alkyl, and n represents an integer of 1 or 2, $R^7$ represents halogen, nitro, cyano, $C_1$-$C_6$-alkyl, hydroxy or $C_1$-$C_6$-alkoxy, wherein $C_1$-$C_6$-alkyl and $C_1$-$C_6$-alkoxy can be further substituted with one to three identical or different radicals selected from the group consisting of halogen, hydroxy and $C_1$-$C_4$-alkoxy, and $Y^1, Y^2, Y^3, Y^4$ and $Y^5$ independently from each other represent CH or N, wherein the ring contains either 0, 1 or 2 nitrogen atoms.

The compounds according to this invention can also be present in the form of their salts, hydrates and/or solvates.

Physiologically acceptable salts are preferred in the context of the present invention.

Physiologically acceptable salts according to the invention are non-toxic salts which in general are accessible by reaction of the compounds (I) with an inorganic or organic base or acid conventionally used for this purpose. Non-limiting examples of pharmaceutically acceptable salts of compounds (I) include the alkali metal salts, e.g. lithium, potassium and sodium salts, the alkaline earth metal salts such as magnesium and calcium salts, the quaternary ammonium salts such as, for example, triethyl ammonium salts, acetates, benzene sulphonates, benzoates, dicarbonates, disulphates, ditartrates, borates, bromides, carbonates, chlorides, citrates, dihydrochlorides, fumarates, gluconates, glutamates, hexyl resorcinates, hydrobromides, hydrochlorides, hydroxynaphthoates, iodides, isothionates, lactates, laurates, malates, maleates, mandelates, mesylates, methylbromides, methylnitrates, methylsulphates, nitrates, oleates, oxalates, palmitates, pantothenates, phosphates, diphosphates, polygalacturonates, salicylates, stearates, sulphates, succinates, tartrates, tosylates, valerates, and other salts used for medicinal purposes.

Hydrates of the compounds of the invention or their salts are stoichiometric compositions of the compounds with water, such as for example hemi-, mono-, or dihydrates.

Solvates of the compounds of the invention or their salts are stoichiometric compositions of the compounds with solvents.

The present invention includes both the individual enantiomers or diastereomers and the corresponding racemates or diastereomeric mixtures of the compounds according to the invention and their respective salts. In addition, all possible tautomeric forms of the compounds described above are included according to the present invention. The diastereomeric mixtures can be separated into the individual isomers by chromatographic processes. The racemates can be resolved into the respective enantiomers either by chromatographic processes on chiral phases or by resolution.

In the context of the present invention, the substituents, if not stated otherwise, in general have the following meaning:

Alkyl in general represents a straight-chain or branched hydrocarbon radical having 1 to 6, preferably 1 to 4 carbon atoms. Non-limiting examples include methyl, ethyl, n-propyl, isopropyl, n-butyl, isobutyl, sec.-butyl, tert-butyl, pentyl, isopentyl, hexyl, isohexyl. The same applies to radicals such as alkoxy, alkylamino, alkoxycarbonyl and alkoxycarbonylamino.

Alkoxy illustratively and preferably represents methoxy, ethoxy, n-propoxy, isopropoxy, tert-butoxy, n-pentoxy and n-hexoxy.

Alkylcarbonyl in general represents a straight-chain or branched hydrocarbon radical having 1 to 6, preferably 1 to 4 carbon atoms which has a carbonyl function at the position of attachment Non-limiting examples include formyl, acetyl, n-propionyl, n-butyryl, isobutyryl pivaloyl, n-hexanoyl.

Alkoxycarbonyl illustratively and preferably represents methoxycarbonyl, ethoxy-carbonyl, n-propoxycarbonyl, isopropoxycarbonyl, tert.-butoxycarbonyl, n-pentoxy-carbonyl and n-hexoxycarbonyl.

Alkylamino represents an alkylamino radical having one or two (independently selected) alkyl substituents, illustratively and preferably representing methylamino, ethylamino, n-propylamino, isopropylamino, tert.-butylamino, n-pentylamino, n-hexyl-amino, N,N-dimethylamino, N,N-diethylamino, N-ethyl-N-methylamino, N-methyl-N-n-propylamino, N-isopropyl-N-n-propylamino, N-tert.-butyl-N-methylamino, N-ethyl-N-n-pentylamino and N-n-hexyl-N-methylamino.

Alkylaminocarbonyl represents an alkylaminocarbonyl radical having one or two (independently selected) alkyl substituents, illustratively and preferably representing methylaminocarbonyl, ethylaminocarbonyl, n-propylaminocarbonyl, isopropylamino-carbonyl, tert.-butylaminocarbonyl, n-pentylaminocarbonyl, n-hexylaminocarbonyl, N,N-dimethylaminocarbonyl, N,N-diethylaminocarbonyl, N-ethyl-N-methylamino-carbonyl, N-methyl-N-n-propylaminocarbonyl, N-isopropyl-N-n-propylaminocarbonyl, N-tert.-butyl- N-methylaminocarbonyl, N-ethyl-N-n-pentylaminocarbonyl and N-n-hexyl-N-methylaminocarbonyl.

Alkylsulfonyl in general represents a straight-chain or branched hydrocarbon radical having 1 to 6, preferably 1 to 4 carbon atoms which has a sulfonyl function at the position of attachment Non-limiting examples include methylsulfonyl ethylsulfonyl, n-propylsulfonyl, isopropylsulfonyl, n-butylsulfonyl, tert-butylsulfonyl.

Cycloalkyl in general represents a cyclic saturated hydrocarbon radical having 3 to 8, preferably 3 to 6 carbon atoms. Non-limiting examples include cyclopropyl, cyclo-butyl, cyclopentyl, cyclohexyl and cycloheptyl.

Aryl per se and in arylcarbonyl represents a mono- to tricyclic aromatic carbocyclic radical having generally 6 to 14 carbon atoms, illustratively and preferably representing phenyl, naphthyl and phenanthrenyl.

Arylcarbonyl illustratively and preferably represents benzoyl and naphthoyl.

Heteroaryl per se and in heteroarylcarbonyl represents an aromatic mono- or bicyclic radical having generally 5 to 10 and preferably 5 or 6 ring atoms and up to 5 and preferably up to 4 heteroatoms selected from the group consisting of S, O and N, illustratively and preferably representing thienyl, furyl, pyrrolyl, thiazolyl oxazolyl imidazolyl, oxadiazolyl, thiadiazolyl, pyridyl, pyrimidyl, pyridazinyl, indolyl, indazolyl, benzofuranyl, benzothiophenyl, benzothiazolyl quinolinyl, isoquinolinyl.

Heteroarylcarbonyl illustratively and preferably represents thienylcarbonyl furyl-carbonyl pyrrolylcarbonyl, thiazolylcarbonyl, oxazolylcarbonyl, imidazolylcarbonyl, pyridylcarbonyl, pyrimidylcarbonyl, pyridazinylcarbonyl, indolylcarbonyl, indazolyl-carbonyl, benzofuranylcarbonyl, benzothiophenylcarbonyl, quinolinylcarbonyl, iso-quinolinylcarbonyl.

Heterocyclyl per se and in heterocyclylcarbonyl represents a mono- or polycyclic, preferably mono- or bicyclic, nonaromatic heterocyclic radical having generally 4 to 10 and preferably 5 to 8 ring atoms and up to 3 and preferably up to 2 heteroatoms and/or hetero groups selected from the group consisting of N, O, S, SO and $SO_2$. The heterocyclyl radicals can be saturated or partially unsaturated. Preference is given to 5- to 8-membered monocyclic saturated heterocyclyl radicals having up to two heteroatoms selected from the group consisting of O, N and S, such as illustratively and preferably tetrahydrofuran-2-yl, pyrrolidin-1-yl, pyrrolidin-2-yl, pyrrolidin-3-yl, pyrrolinyl, piperidinyl, morpholinyl perhydroazepinyl.

Heterocyclylcarbonyl illustratively and preferably represents tetrahydrofuran-2-carbonyl, pyrrolidine-1-carbonyl, pyrrolidine-2-carbonyl, pyrrolidine-3-carbonyl, pyrrolinecarbonyl, piperidinecarbonyl, morpholinecarbonyl, perhydroazepine-carbonyl.

Halogen represents fluorine, chlorine, bromine and iodine.

When stated, that $Y^1, Y^2, Y^3, Y^4$ and $Y^5$ represent CH or N, CH shall also stand for a ring carbon atom, which is substituted with a substituent $R^3$ or $R^7$.

A * symbol next to a bond denotes the point of attachment in the molecule.

In another embodiment, the present invention relates to compounds of general formula (I), wherein A represents an aryl or heteroaryl ring, $R^1$, $R^2$ and $R^3$ independently from each other represent hydrogen, halogen, nitro, cyano, $C_1$-$C_6$-alkyl, hydroxy or $C_1$-$C_6$-alkoxy, wherein $C_1$-$C_6$-alkyl and $C_1$-$C_6$-alkoxy can be further substituted with one to three identical or different radicals selected from the group consisting of halogen, hydroxy and $C_1$-$C_4$-alkoxy, $R^4$ represents $C_1$-$C_6$-alkylcarbonyl, $C_1$-$C_6$-alkoxycarbonyl, $C_1$-$C_6$-alkenoxy-carbonyl, hydroxycarbonyl, aminocarbonyl, mono- or di-$C_1$-$C_4$-alkylamino-carbonyl, $C_6$-$C_{10}$-arylaminocarbonyl, heteroarylcarbonyl, heterocyclyl-carbonyl, heteroaryl, heterocyclyl or cyano, wherein $C_1$-$C_6$-alkylcarbonyl, $C_1$-$C_6$-alkoxycarbonyl, mono- and di-$C_1$-$C_4$-alkylaminocarbonyl can be further substituted with one to three identical or different radicals selected from the group consisting of $C_3$-$C_8$-cycloalkyl, hydroxy, $C_1$-$C_4$-alkoxy, $C_1$-$C_4$-alkoxycarbonyl, hydroxycarbonyl aminocarbonyl, mono- and di-$C_1$-$C_4$-alkylaminocarbonyl, $C_1$-$C_4$-alkylcarbonylamino, amino, mono- and di-$C_1$-$C_4$-alkylamino, heteroaryl, heterocyclyl and tri-($C_1$-$C_6$-alkyl)-silyl, $R^5$ represents $C_1$-$C_4$-alkyl, which can be substituted with one to three identical or different radicals selected from the group consisting of halogen, hydroxy, $C_1$-$C_6$-alkoxy, $C_1$-$C_6$-alkenoxy, $C_1$-$C_6$-alkylthio, amino, mono- and di-$C_1$-$C_6$-alkylamino, arylamino, hydroxycarbonyl, $C_1$-$C_6$-alkoxycarbonyl and the radical —O—$C_1$-$C_4$-alkyl-O—$C_1$-$C_4$-alkyl, or $R^5$ represents amino, $R^6$ represents hydrogen, $C_1$-$C_6$-alkyl, formyl, aminocarbonyl, mono- or di-$C_1$-$C_4$-alkylaminocarbonyl, $C_3$-$C_8$-cycloalkylcarbonyl, $C_1$-$C_6$-alkylcarbonyl, $C_1$-$C_6$-alkoxycarbonyl, N—($C_1$-$C_4$-alkylsulfonyl)-aminocarbonyl, N—($C_1$-$C_4$-alkylsulfonyl)-N—($C_1$-$C_4$-alkyl)-aminocarbonyl, heteroaryl, heterocyclyl, hetero-arylcarbonyl or heterocyclylcarbonyl, wherein $C_1$-$C_6$-alkyl, mono- and di-$C_1$-$C_4$-alkylaminocarbonyl, $C_1$-$C_6$-alkylcarbonyl, $C_1$-$C_6$-alkoxycarbonyl, heteroaryl and heterocyclyl can be substituted with one to three identical or different radicals selected from the group consisting of aryl, heteroaryl, hydroxy, $C_1$-$C_4$-alkoxy, hydroxycarbonyl, $C_1$-$C_6$-alkoxycarbonyl, amino-carbonyl, mono- and di-$C_1$-$C_4$-alkylaminocarbonyl, amino, mono- and di-$C_1$-$C_4$-alkylamino, $C_1$-$C_4$-alkylcarbonylamino, tri-($C_1$-$C_6$-alkyl)-silyl, cyano, N-(mono- and di-$C_1$-$C_4$-alkylamino-$C_1$-$C_4$-alkyl)-aminocarbonyl, N—($C_1$-$C_4$-alkoxy-$C_1$-$C_4$-alkyl)-aminocarbonyl and halogen, or $R^6$ represents a moiety of the formula

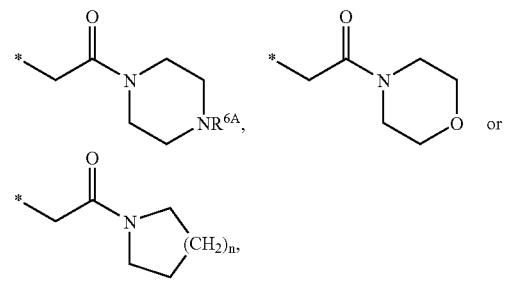

wherein $R^{6A}$ is selected from the group consisting of hydrogen and $C_1$-$C_6$-alkyl, and n represents an integer of 1 or 2, $R^7$ represents halogen, nitro, cyano, $C_1$-$C_6$-alkyl, hydroxy or $C_1$-$C_6$-alkoxy, wherein $C_1$-$C_6$-alkyl- and $C_1$-$C_6$-alkoxy can be further substituted with one to three identical or different radicals selected from the group consisting of halogen, hydroxy and $C_1$-$C_4$-alkoxy, and Y$^1$, Y$^2$, Y$^3$, Y$^4$ and Y$^5$ independently from each other represent CH or N, wherein the ring contains either 0, 1 or 2 nitrogen atoms.

In another embodiment, the present invention relates to compounds of general formula (I), wherein A represents a phenyl, naphthyl or pyridyl ring, R$^1$, R$^2$ and R$^3$ independently from each other represent hydrogen, fluoro, chloro, bromo, nitro, cyano, methyl, ethyl, trifluoromethyl or trifluoromethoxy, R$^4$ represents C$_1$-C$_6$-alkylcarbonyl, C$_1$-C$_6$-alkoxycarbonyl hydroxycarbonyl, aminocarbonyl, mono-C$_1$-C$_4$-alkylaminocarbonyl or cyano, wherein C$_1$-C$_6$-alkylcarbonyl, C$_1$-C$_6$-alkoxycarbonyl and mono-C$_1$-C$_4$-alkylaminocarbonyl can be substituted with one to three identical or different radicals selected from the group consisting of C$_3$-C$_8$-cycloalkyl, hydroxy, C$_1$-C$_4$-alkoxy, C$_1$-C$_4$-alkoxycarbonyl, ammo, mono- or di-C$_1$-C$_4$-alkylamino, heteroaryl and heterocyclyl, R$^5$ represents methyl or ethyl, R$^6$ represents hydrogen, C$_1$-C$_6$-alkyl, mono- or di-C$_1$-C$_4$-alkylaminocarbonyl C$_1$-C$_6$-alkylcarbonyl, C$_1$-C$_6$-alkoxycarbonyl or heterocyclylcarbonyl, wherein C$_1$-C$_6$-alkyl and C$_1$-C$_6$-alkoxycarbonyl can be substituted with one to three identical or different radicals selected from the group consisting of heteroaryl, hydroxy, C$_1$-C$_4$-alkoxy, hydroxycarbonyl, C$_1$-C$_6$-alkoxycarbonyl, amino-carbonyl, mono- and di-C$_1$-C$_4$-alkylaminocarbonyl, cyano, amino, mono- and di-C$_1$-C$_4$-alkylamino, or R$^6$ represents a moiety of the formula

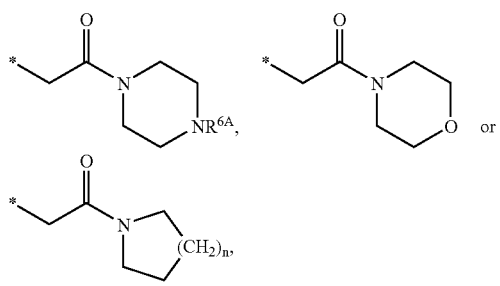

wherein

R$^{6A}$ is selected from the group consisting of hydrogen and C$_1$-C$_4$-alkyl, and n represents an integer of 1 or 2, R$^7$ represents halogen, nitro, cyano, trifluoromethyl, trifluoromethoxy, methyl or ethyl, and Y$^1$, Y$^2$, Y$^3$, Y$^4$ and Y$^5$ each represent CH.

In another embodiment, the present invention relates to compounds of general formula (I), wherein A represents a phenyl or a pyridyl ring, R$^1$ and R$^3$ each represent hydrogen, R$^2$ represents fluoro, chloro, bromo, nitro or cyano, R$^4$ represents cyano, C$_1$-C$_4$-alkylcarbonyl or C$_1$-C$_4$-alkokycarbonyl, wherein C$_1$-C$_4$-alkoxycarbonyl can be substituted with a radical selected from the group consisting of hydroxy, C$_1$-C$_4$-alkoxy, C$_1$-C$_4$-alkoxycarbonyl, mono- and di-C$_1$-C$_4$-alkylamino, heteroaryl and heterocyclyl, R$^5$ represents methyl, R$^6$ represents hydrogen, C$_1$-C$_4$-alkyl, mono- or di-C$_1$-C$_4$-alkylaminocarbonyl, C$_1$-C$_4$-alkylcarbonyl or C$_1$-C$_4$-alkoxycarbonyl, wherein C$_1$-C$_4$-alkyl and C$_1$-C$_4$-alkoxycarbonyl can be substituted with a radical selected from the group consisting of heteroaryl, hydroxy, C$_1$-C$_4$-alkoxy, hydroxycarbonyl, aminocarbonyl, mono- and di-C$_1$-C$_4$-alkylaminocarbonyl, amino, mono- and di-C$_1$-C$_4$-alkylamino, or R$^6$ represents a moiety of the formula

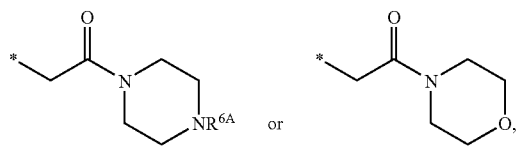

wherein

R$^{6A}$ is selected from the group consisting of hydrogen and methyl,

R$^7$ represents trifluoromethyl or nitro, and

Y$^1$, Y$^2$, Y$^3$, Y$^4$ and Y$^5$ each represent CH.

In another embodiment, the present invention relates to compounds according to general formula (I), wherein A is phenyl or pyridyl.

In another embodiment, the present invention relates to compounds according to general formula (I), wherein R$^1$ is hydrogen.

In another embodiment, the present invention relates to compounds according to general formula (I), wherein R$^2$ is cyano, especially wherein A is phenyl or pyridyl and R$^2$ is cyano located in para-position relative to the central dihydropyrimidinone ring.

In another embodiment, the present invention relates to compounds according to general formula (I), wherein R$^3$ is hydrogen.

In another embodiment, the present invention relates to compounds according to general formula (I), wherein R$^4$ is C$_1$-C$_4$-alkoxycarbonyl optionally substituted by hydroxy, especially 2-hydroxyethoxycarbonyl, or wherein R$^4$ is C$_1$-C$_4$-alkylcarbonyl, especially methylcarbonyl.

In another embodiment, the present invention relates to compounds according to general formula (I), wherein R$^5$ is methyl.

In another embodiment, the present invention relates to compounds according to general formula (I), wherein R$^6$ is hydrogen.

In another embodiment, the present invention relates to compounds according to general formula (I), wherein R$^7$ is trifluoromethyl or nitro, especially wherein R$^7$ is trifluoromethyl located in meta-position relative to the central dihydropyrimidinone ring.

In another embodiment, the present invention relates to compounds of general formula (IA)

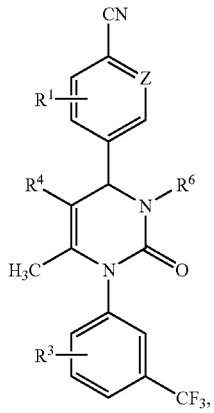

(IA)

wherein
Z represents CH or N, and
$R^1$, $R^3$, $R^4$ and $R^6$ have the meaning indicated above.

The compounds of the present invention, wherein $R^6$ is hydrogen, can enolize into the corresponding hydroxyamidines:

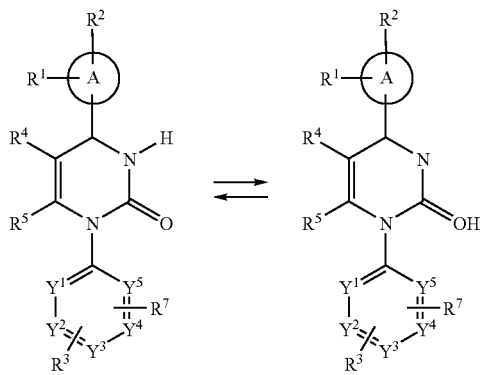

The compounds of general formula (I) can be synthesized by condensing compounds of general formula (II)

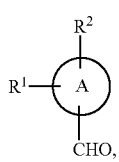

(II)

wherein
A, $R^1$ and $R^2$ have the meaning indicated above,
with compounds of general formula (III)

(III)

wherein
$R^4$ and $R^5$ have the meaning indicated above,
and compounds of general formula (W)

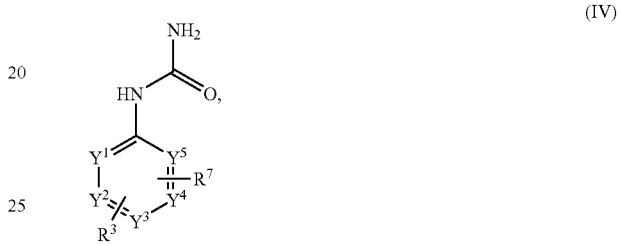

(IV)

wherein
$R^3$, $R^7$, and $Y^1$ to $Y^5$ have the meaning indicated above, in the presence of an acid either in a three-component/one-step reaction or sequentially to give compounds of the general formula (IB)

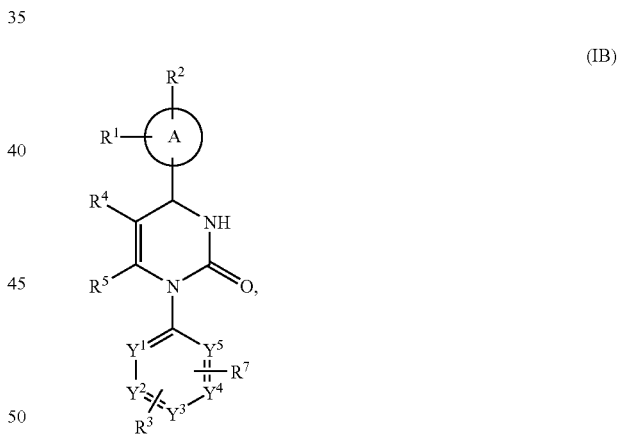

(IB)

wherein
A, $R^1$ to $R^5$, $R^7$, and $Y^1$ to $Y^5$ have the meaning indicated above, optionally followed by reaction of the compounds of general formula (IB) with compounds of the general formula (V)

$R^{6*}$—X   (V), wherein
$R^{6*}$ has the meaning of $R^6$ as indicated above, but does not represent hydrogen, and
X represents a leaving group, such as halogen, tosylate, mesylate or sulfate, in the presence of a base.

The compounds of general formula (I), wherein $R^4$ represents cyano, $R^5$ represents amino and $R^6$ represents hydrogen, can alternatively be prepared by condensing compounds of general formula (II) with compounds of general formula (I) and a compound of formula (VI)

NC—CH$_2$—CN      (VI)

in the presence of an acid either in a three-component/one-step reaction or sequentially.

Suitable solvents for the process (II)+(III)/(VI)+(V)→(IB) are generally customary organic solvents which do not change under the reaction conditions. These include ethers such as diethyl ether, diisopropyl ether, 1,2-dimethoxyethane, dioxan or tetrahydrofuran, ethyl acetate, acetone, acetonitrile, dimethylsulfoxide, dimethyl-formamide, or alcohols such as methanol, ethanol, n-propanol, isopropanol n-butanol or t-butanol, or hydrocarbons such as pentane, hexane, cyclohexane, benzene, toluene or xylene, or halogeno-hydrocarbons such as dichloromethane, dichloroethane, trichloromethane or chlorobenzene. It is also possible to use mixtures of the above-mentioned solvents. Preferred for the process is tetrahydrofuran.

Suitable acids for the process (II)+(III)/(VI)+(IV)→(IB) are generally inorganic or organic acids. These preferably include carboxylic acids, such as, for example, acetic acid or trifluoroacetic acid, sulfonic acids, such as, for example, methanesulfonic acid or p-toluenesulfonic acid, hydrochloric acid or phosphoric acids such as polyphosphoric acids. Preference is given to polyphosphoric acid ethyl ester. The acid is employed in an amount from 0.25 mol to 100 mol, relative to 1 mol of the compound of the general formula (III).

The process is in general carried out in a temperature range from +20° C. to +150° C., preferably from +60° C. to +100° C.

The process is generally carried out at normal pressure. However, it is also possible to carry it out at elevated pressure or at reduced pressure (for example in a range from 0.5 to 5 bar).

Suitable solvents for the process (IB)+(V)→(I) are generally customary organic solvents which do not change under the reaction conditions. These include ethers such as diethyl ether, diisopropyl ether, 1,2-dimethoxyethane, dioxan or tetra-hydrofuran, ethyl acetate, acetone, acetonitrile, dimethylsulfoxide, dimethylformamide, or hydrocarbons such as pentane, hexane, cyclohexane, benzene, toluene or xylene, or halogeno-hydrocarbons such as dichloromethane, dichloroethane, tri-chloromethane or chlorobenzene. It is also possible to use mixtures of the above-mentioned solvents. Preferred for the process is tetrahydrofuran.

Suitable bases for the process (IB)+(V)→(I) are generally inorganic or organic bases. These preferably include cyclic amines, such as, for example, piperidine or 4-N,N-dimethylaminopyridine, or ($C_1$-$C_4$)-trialkylamines, such as, for example, triethylamine or diisopropylethylamine, or hydrides such as sodium hydride. Preference is given to sodium hydride. The base is employed in an amount from 0.1 mol to 10 mol, preferably from 1 mol to 3 mol, relative to 1 mol of the compound of general formula (I).

The process is in general carried out in a temperature range from 0° C. to +150° C., preferably from +20° C. to +80° C., especially at room temperature.

The process is generally carried out at normal pressure. However, it is also possible to carry it out at elevated pressure or at reduced pressure (for example in a range from 0.5 to 5 bar).

The compounds of the general formulas (II), (II), (IV), (V) and (VI) are known per se, or they can be prepared by customary methods.

The above-mentioned method can be illustrated by the following scheme:

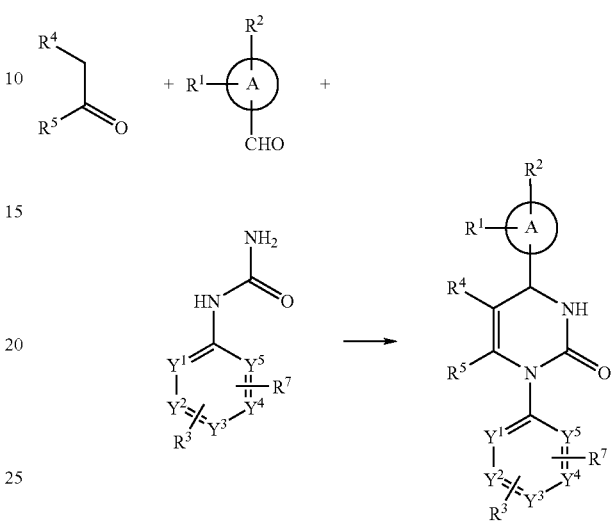

The compounds according to the invention exhibit an unforeseeable, useful pharmacological and pharmacokinetic activity spectrum. They are therefore suitable for use as medicaments for the treatment and/or prophylaxis of disorders in humans and animals.

Surprisingly, the compounds of the present invention show human neutrophil elastase (HNE) inhibitory activity and are therefore suitable for the preparation of medicaments for the treatment of diseases associated with HNE activity. They may thus provide an effective treatment of acute and chronic inflammatory processes, such as rheumatoid arthritis, atherosclerosis, and especially of acute and chronic pulmonary diseases, such as lung fibrosis, cystic fibrosis, pneumonia, acute respiratory distress syndrome (ARDS), in particular pulmonary emphysema, including smoking-induced emphysema, and chronic obstructive pulmonary diseases (COPD), chronic bronchitis and bronchiectasis. The compounds of the present invention may further provide an effective treatment for cardiovascular ischaemic diseases such as acute coronary syndrome, acute myocardial infarction, unstable and stable angina pectoris, coronary artery bypass grafts (CABG) and heart failure development, for atherosclerosis, mitral valvular disease, atrial septal defects, percutaneous transluminal coronary angioplasty (PTCA), inflammation after open heart surgery and for pulmonary hypertension. They may also prove useful for an effective treatment of rheumatoid arthritis, acute inflammatory arthritis, cancer, acute pancreatitis, ulcerative colitis, periodontal disease, Chury-Strauss syndrome, acute and chronic atopic dermatitis, psoriasis, systemic lupus erythematosus, bullous pemphigus, sepsis, alcoholic hepatitis, liver fibrosis, Behcet's disease, allergic fungal sinusitis, allergic sinusitis, Crohn's disease, Kawasaki disease, glomerulonephritis, acute pyelonephritis, colorectal diseases, chronic suppurative otitis media, chronic venous leg ulcers, inflammatory bowel disease, bacterial and viral infections, brain trauma, stroke and other conditions in which neutrophil participation is involved.

The present invention further provides medicaments containing at least one compound according to the invention, preferably together with one or more pharmacologically safe excipient or carrier substances, and also their use for the above-mentioned purposes.

The active component can act systemically and/or locally. For this purpose, it can be applied in a suitable manner, for example orally, parenterally, pulmonally, nasally, sublingually, lingually, buccally, rectally, transdermally, conjunctivally, otically or as an implant.

For these application routes, the active component can be administered in suitable application forms.

Useful oral application forms include application forms which release the active component rapidly and/or in modified form, such as for example tablets (non-coated and coated tablets, for example with an enteric coating), capsules, sugar-coated tablets, granules, pellets, powders, emulsions, suspensions, solutions and aerosols.

Parenteral application can be carried out with avoidance of an absorption step (intravenously, intraarterially, intracardially, intraspinally or intralumbarly) or with inclusion of an absorption (intramuscularly, subcutaneously, intracutaneously, percutaneously or intraperitoneally). Useful parenteral application forms include injection and infusion preparations in the form of solutions, suspensions, emulsions, lyophilisates and sterile powders.

Forms suitable for other application routes include for example inhalatory pharmaceutical forms (including powder inhalers, nebulizers), nasal drops/solutions, sprays; tablets or capsules to be administered lingually, sublingually or buccally, suppositories, ear and eye preparations, vaginal capsules, aqueous suspensions (lotions, shake mixtures), lipophilic suspensions, ointments, creams, milk, pastes, dusting powders or implants.

The active components can be converted into the recited application forms in a manner known per se. This is carried out using inert non-toxic, pharmaceutically suitable excipients. These include inter alia carriers (for example microcrystalline cellulose), solvents (for example liquid polyethylene glycols), emulsifiers (for example sodium dodecyl sulphate), dispersing agents (for example polyvinyl-pyrrolidone), synthetic and natural biopolymers (for example albumin), stabilizers (for example antioxidants such as ascorbic acid), colorants (for example inorganic pigments such as iron oxides) or taste and/or odor corrigents.

For human use, in the case of oral administration, it is recommendable to administer doses of from 0.001 to 50 mg/kg, preferably of 0.01 mg/kg to 20 mg/kg. In the case of parenteral administration, such as, for example, intravenously or via mucous membranes nasally, buccally or inhalationally, it is recommendable to use doses of 0.001 mg/kg to 0.5 mg/kg.

In spite of this, it can be necessary in certain circumstances to depart from the amounts mentioned, namely as a function of body weight, application route, individual behaviour towards the active component, manner of preparation and time or interval at which application takes place. It can for instance be sufficient in some cases to use less than the aforementioned minimum amount, while in other cases the upper limit mentioned will have to be exceeded. In the case of the application of larger amounts, it can be advisable to divide them into a plurality of individual doses spread through the day.

The percentages in the tests and examples which follows are, unless otherwise stated, by weight; parts are by weight. Solvent ratios, dilution ratios and concentrations reported for liquid/liquid solutions are each based on the volume.

A. EVALUATION OF PHYSIOLOGICAL ACTIVITY

The potential of the compounds of the invention to inhibit neutrophil elastase activity may be demonstrated, for example, using the following assays:

I. In vitro Enzyme Assays of Human Neutrophil Elastase (HNE)

Assay Contents assay buffer: 0.1 M HEPES-NaOH buffer pH 7.4, 0.5 M NaCl, 0.1% (w/v) bovine serum albumin;

suitable concentration (see below) of HNE (18 U/mg lyophil., #20927.01, SERVA Electrophoresis GmbH, Heidelberg, Germany) in assay buffer;

suitable concentration (see below) of substrate in assay buffer;

suitable concentration of test compounds diluted with assay buffer from a 10 mM stock solution in DMSO.

Example A

In Vitro Inhibition of HNE Using a Fluorogenic Peptide Substrate (Continuous Read-Out Signal, 384 MTP Assay Format):

In this protocol, the elastase substrate MeOSuc-Ala-Ala-Pro-Val-AMC (#324740, Calbiochem-Novabiochem Corporation, Merck KGaA, Darmstadt, Germany) is used. The test solution is prepared by mixing 10 µl of test compound dilution, 20 µl of HNE enzyme dilution (final concentration 8-0.4 µU/ml, routinely 2.1 µU/ml) and 20 µl of substrate dilution (final concentration 1 mM-1 µM, routinely 20 µM), respectively. The solution is incubated for 0-2 hrs at 37° C. (routinely one hour). The florescence of the liberated AMC due to the enzymatic reaction is measured at 37° C. (TECAN spectra fluor plus plate reader). The rate of increase of the fluorescence (ex. 395 nm, em 460 nm) is proportional to elastase activity. $IC_{50}$ values are determined by RFU-versus-[I] plots. $K_m$ and $K_{m(app.)}$ values are determined by Lineweaver-Burk inverted to $K_i$ values by Dixon plots.

The preparation examples had $IC_{50}$ values within the range of 5 nM-5 µM in this assay. Representative data are given in Table 1:

TABLE 1

| Example No. | $IC_{50}$ [nM] |
|---|---|
| 1 | 8 |
| 9 | 40 |
| 14 | 5 |
| 15 | 8 |
| 16 | 10 |
| 20 | 700 |
| 24 | 13 |
| 26 | 10 |
| 28 | 50 |
| 58 | 1100 |
| 60 | 5 |
| 72 | 6 |
| 73 | 60 |
| 74 | 20 |
| 103 | 60 |
| 109 | 15 |
| 110 | 50 |

Example B

In Vitro Inhibition of HNE Using a Fluorogenic, Unsoluble Elastin Substrate (Discontinuous Read-Out Signal, 96 MTP Assay Format):

In this protocol the elastase substrate elastin-fluorescein (#100620, ICN Biomedicals GmbH, Eschwege, Germany) is used. The test solution is prepared by mixing 3 μl of test compound dilution, 77 μl of HNE enzyme dilution (final concentration 0.22 U/ml-2.2 mU/ml, routinely 21.7 μU/ml) and 80 μl substrate suspension (final concentration 2 mg/ml). The suspension is incubated for 0-16 hrs at 37° C. (routinely four hours) under slightly shaking conditions. To stop the enzymatic reaction, 160 μl of 0.1 M acetic acid are added to the test solution (final concentration 50 mM); The polymeric elastin-fluorescein is pulled down by centrifugation (Eppendorf 5804 centrifuge, 3.000 rpm, 10 min). The supernatant is transferred into a new MTP and the fluorescence of the liberated peptide fluorescein due to the enzymatic reaction is measured (BMG Fluostar plate reader). The rate of fluorescence (ex. 490 nm, em. 520 nm) is proportional to elastase activity. $IC_{50}$ values are determined by RFU-versus-[I] plots.

II. In Vitro Human Neutrophil Assays

Example A

In Vitro PMN Elastolysis Assay:

This assay is used to determine the elastolytic potential of human polymorphonuclear cells (PMNs) and assess the proportion of degradation due to neutrophil elastase [cf. Z. W. She et al., Am. J. Respir. Cell. Mol. Biol. 9, 386-392 (1993)].

Tritiated elastin, in suspension, is coated on to a 96 well plate at 10 μg per well. Test and reference [ZD-0892 (J. Med. Chem. 40, 1876-1885, 3173-3181 (1997), WO 95/21855) and α1 protease inhibitor (α1PI)] compounds are added to the wells at the appropriate concentrations. Human PMNs are separated from peripheral venous blood of healthy donors and resuspended in culture media The neutrophils are added to the coated wells at concentrations ranging between $1 \times 10^6$ to $1 \times 10^5$ cells per well. Porcine pancreatic elastase (1.3 μM is used as a positive control for the assay, and α1PI (1.2 μM) is used as the positive inhibitor of neutrophil elastase. The cellular control is PMNs without compound at each appropriate cell density. The cells plus compounds are incubated in a humidified incubator at 37° C. for 4 hours. The plates are centrifuged to allow the harvest of cell supernatant only. The supernatant is transferred in 75 μl volumes to corresponding wells of a 96 well Lumaplate™ (solid scintillant containing plates). The plates are dried until no liquid is visible in the wells and read in a beta counter for 3 minutes per well.

Elastolysis of the $^3$H-elastin results in an increase in counts in the supernatant. An inhibition of this elastolysis shows a decrease, from the cellular control, of tritium in the supernatant. α1PI gave 83.46±3.97% (mean±s.e.m.) inhibition at 1.2 μM (n=3 different donors at $3.6 \times 10^5$ cells per well). $IC_{50}$ values, were obtained for the reference compound ZD-0892 of 45.50±7.75 nM (mean±s.e.m.) (n=2 different donors at $3.6 \times 10^5$ cells per well).

Given that ZD-0892 is a selective inhibitor of PMN elastase along with the data from α1PI inhibition, these results indicate that the majority of elastin degradation by PMNs is due to the release of neutrophil elastase, and not to another elastolytic enzyme such as matrix metalloproteases (MMPs). The compounds of this invention are evaluated for their inhibitory activity in this HNE-dependent model of neutrophil elastolysis.

Example B

In Vitro Inhibition of Membrane Bound Elastase:

Measurement of the inhibition of elastase bound to neutrophil membranes is performed using a human neutrophil assay. Neutrophils are stimulated with LPS at 37° C. for 35 min and then spun at 1600 rpm. Subsequently, the membrane bound elastase is fixed to the neutrophils with 3% paraformaldehyde and 0.25% glutaraldehyde for 3 min at 4° C. The neutrophils are then spun, and vehicle and the compound under evaluation are added, followed by addition of the substrate MeO-Suc-Ala-Ala-Pro-Val-AMC (#324740, Calbiochem-Novabiochem Corporation, Merck KGaA, Darmstadt, Germany) at 200 μM. Following a 25 min incubation at 37° C., the reaction is terminated with PMSF (phenylmethanesulfonyl fluoride), and the fluorescence is read at ex: 400 nm and em: 505 nm. $IC_{50}$ values are determined by interpolation from plots of relative fluorescence vs. inhibitor concentration.

III. In Vivo Models

Example A

In Vivo Model of Acute Lung Injury in the Rat:

Instillation of human neutrophil elastase (HNE) into rat lung causes acute lung damage. The extent of this injury can be assessed by measuring lung hemorrhage.

Rats are anaesthetised with Hypnorm/Hypnovel/water and instilled with HNE or saline delivered by microsprayer into the lungs. Test compounds are administered by intravenous injection, by oral gavage or by inhalation at set times prior to the administration of HNE. Sixty minutes after the administration of elastase animals are killed by an anaesthetic overdose (sodium pentobarbitone) and the lungs lavaged with 2 ml heparinised phosphate buffered saline (PBS). Bronchoalveolar lavage (BAL) volume is recorded and the samples kept on ice. Each BAL sample is centrifuged at 900 r.p.m. for 10 minutes at 4-10° C. The supernatant is discarded and the cell pellet resuspended in PBS and the sample spun down again. The supernatant is again discarded and the cell pellet resuspended in 1 ml 0.1% cetyltrimethyl-ammonium bromide (CTAB)/PBS to lyse the cells. Samples are frozen until blood content is assayed. Prior to the hemorrhage assay the samples are defrosted and mixed. 100 μl of each sample are placed into a separate well of a 96 well flat-bottomed plate. All samples are tested in duplicate. 100 μl 0.1% CTAB/PBS is included as a blank. The absorbance of the well contents is measured at 415 nm using a spectrophotometer. A standard curve is constructed by measuring the OD at 415 nm of different concentrations of blood in 0.1% CTAB/PBS. Blood content values are calculated by comparison to the standard curve (included in each plate) and normalised for the volume of BAL fluid retrieved.

The compounds of this invention are evaluated intravenously, orally or by inhalation for their inhibitory activity in this model of HNE-induced hemorrhage in the rat.

Example B

In Vivo Model of Acute Myocardial Infarction in the Rat:

Elastase inhibitors are tested in a rat thread infarct model. Male Wistar rats (weighing >300 g) receive 10 mg/kg aspirin 30 min prior to surgery. They are anaesthetized by isofluran and ventilated (120-130 strokes/min, 200-250 μl stroke volume; MiniVent Type 845, Hugo Sachs Elektronik, Germany) during the whole surgery. Following a left thoracotomy at the fourth intercostal space, the pericardium is opened and the heart briefly exteriorized. A thread is turned around the left coronary artery (LAD) without occluding the artery. The thread is passed under the skin to the neck of the animal. The thorax is closed and the animal is allowed to recover for 4 days. At the fifth day, rats are anaesthetized with ether for 3 min, and the thread is tied and the LAD occluded under ECG control. Test compounds are administered before or after LAD occlusion per os, intraperitoneally or intravenously (bolus or permanent infusion). After 1 hr occlusion, the thread is reopened to allow reperfusion. Hearts are excised, and infarct sizes are determined 48 hours later by staining of the re-occluded hearts with Evans blue, followed by TTC (triphenyltetrazolium chloride) staining of 2 mm heart sections. Normoxic (not occluded tissue) areas stain blue, ischemic (occluded but surviving tissue) areas stain red and necrotic (occluded dead tissue) areas remain white. Each tissue section is scanned and infarct sizes are determined by computer planimetry.

B. EXAMPLES

Abbreviations aq. aqueous
conc. concentrated
DMF N,N-dimethylformamide
DMSO dimethylsulfoxide
EI electron impact ionisation (for MS)
ESI electro-spray ionisation (for MS)
HPLC high pressure liquid chromatography
LC-MS liquid chromatography coupled with mass spectroscopy
Mp. melting point
MS mass spectroscopy
NMR nuclear magnetic resonance spectroscopy
of th. of theoretical (yield)
$R_t$ retention time (for HPLC)
THF tetrahydrofuran General Methods:

All reactions are carried out under an argon atmosphere unless otherwise noted. Solvents are used as purchased from Aldrich without further purification. 'Silica gel' or 'Silica' refers to Silica gel 60 (0.040 mm-0.063 mm) from Merck KGaA company. Melting points were obtained with a Büchi 512 or similar melting point device and are uncorrected.

Compounds purified by preparative HPLC are purified over a RP18-column with acetonitrile and water as the eluent, using a 1:9 to 9:1 gradient.

LC-MS/HPLC Methods:

LC-MS Method 1

Instrument: Micromass Quattro LCZ, HP1100; column: Uptisphere HDO, 50 mm×2.0 mm, 3 µm; eluent A: water+0.05% formic acid, eluent B: acetonitrile+0.05% formic acid; gradient: 0.0 min 100% A→0.2 min 100% A→2.9 min 30% A→3.1 min 10% A→4.5 min 10% A; oven: 55° C.; flow: 0.8 ml/min; UV-detection: 208-400 nm.

LC-MS Method 2

Instrument: Waters Alliance 2790 LC; column: Symmetry C18, 50 mm×2.1 mm, 3.5 µm; eluent A: water+0.1% formic acid, eluent B: acetonitrile+0.1% formic acid; gradient: 0.0 mm 5% B→5.0 min 10% B→6.0 min 10% B; temperature: 50° C.; flow: 1.0 ml/min; UV-detection: 210 nm.

LC-MS Method 3

Instrument: Micromass Platform LCZ, HP1100; column: Aquasil C-18, 50 mm×2.0 mm, 3 µm; eluent A: water+0.05% formic acid, eluent B: acetonitrile+0.05% formic acid; gradient: 0.0 min 100% A→0.2 min 100% A→2.9 min 30% A→3.1 min 10% A→4.5 min 10% A; oven: 55° C.; flow: 9.8 ml/min; UV-detection: 208-400 nm.

HPLC Method 4

Instrument: HP 1100 with DAD-detection; column: Kromasil RP-18, 60 mm×2 mm, 3.5 µm; eluent: A=5 ml $HClO_4$/l $H_2O$, B=acetonitrile; gradient: 0 min 2% B, 0.5 min 2% B, 4.5 min 90% B, 6.5 min 90% B; flow: 0.75 ml/min; temperature: 30° C.; UV-detection: 210 nm.

LC-MS Method 5

Instrument: Micromass TOF-MUX-Interface 4-fold parallel injection, with HPLC Waters 600; column: Uptisphere HDO, 50 mm×2.0 mm, 3.0 µm; eluent A: 1 l water+1 ml 50% formic acid, eluent B: 1 l acetonitrile+1 ml 50% formic acid, gradient: 0.0 min 100% A→0.2 min 100% A→2.9 min 30% A→3.1 min 10% A→4.5 min 10% A→4.6 min 100% A→6.5 min 100% A; oven: room temperature; flow: 0.8 ml/min; UV-detection: 210 nm.

LC-MS Method 6

Instrument: Micromass Platform LCZ with HPLC Agilent Serie 1100; column: Grom-SIL120 ODS-4 HE, 50 mm×2.0 mm, 3 µm; eluent A: 1 l water+1 ml 50% formic acid, eluent B: 1 l acetonitrile+1 ml 50% formic acid; gradient: 0.0 min 100% A→0.2 min 100% A→2.9 min 30% A→3.1 min 10% A→4.5 min 10% A; oven: 55° C.; flow: 0.8 ml/min; UV-detection: 208-400 nm.

LC-MS Method 7

Instrument: Micromass Quattro LCZ with HPLC Agilent Serie 1100; column: Uptisphere HDO, 50 mm×2.0 mm, 3 µm; eluent A: 1 l water+1 ml 50% formic acid, eluent B: 1 l acetonitrile+1 ml 50% formic acid; gradient: 0.0 min 100% A→0.2 min 100% A→2.9 min 30% A→3.1 min 10% A→4.5 min 10% A; oven: 55° C.; flow: 0.8 ml/min; WV-detection: 208-400 nm.

Starting Materials:

Example 1A

2-Bromo-5-(1,3-dioxolan-2-yl)pyridine

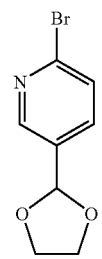

6-Bromo-3-pyridinecarbaldehyde (500 mg, 2.7 mmol) and 1,2-ethanediol (200 mg, 3.2 mmol) are dissolved in toluene (50 ml) together with Amberlyst 15 (100 mg) in a round bottom flask equipped with a reflux condenser and a Dean-Stark trap. The solution is stirred at reflux overnight, then cooled to room temperature, filtered and concentrated in vacuo. The crude product is chromatographed over silica gel with cyclohexane and ethyl acetate as the eluent to afford the title compound as a colorless oil.

Yield: 0.489 g (79% of th.)
HPLC (method 4): 3.46 min.
MS (ESIpos): m/z=231 (M+H)$^+$ ¹H-NMR (300 MHz, CDCl₃): δ=8.46 (d, 1H), 7.64 (m, 1H), 7.49 (m, 1H), 4.15-4.00 (m, 4H) ppm.

Example 2A 5-(1,3-Dioxolan-2-yl)-2-pyridinecarbonitrile

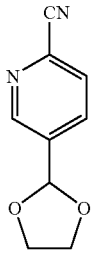

Example 1A (2.8 g, 12.5 mmol), zinc cyanide (1.6 g, 13.8 mmol) and tetrakis-(triphenylphosphine)palladium(0) (1.4 g, 1.3 mmol) are dissolved in dimethyl-formamide (100 ml) and stirred overnight (18 h) at 80° C. Additional tetrakis-(triphenylphosphine)palladium(0) (0.1 g) is added and the reaction is stirred again overnight (18 h) at 80° C., then allowed to stand at room temperature for 2 days (48 hours). The solvent is removed in vacuo, to the residue is given water (100 ml) and the product is extracted with ethyl acetate (1 l). The organic phase is washed with brine (200 ml), dried with magnesium sulphate monohydrate, filtered and concentrated in vacuo. The crude product is chromatographed over silica gel with cyclohexane and ethyl acetate as the eluent to afford the title compound as a white amorphous solid.

Yield: 0.94 g (42% of th.)
HPLC (method 4): 3.21 min.
MS (ESIpos): m/z=177 (M+H)⁺
¹H-NMR (400 MHz, DMSO-d₆): δ=8.81 (s, 1H), 8.09 (s, 2H), 5.95 (s, 1H), 4.13-3.94 (m, 4H) ppm.

Example 3A

5-Formyl-2-pyridinecarbonitrile

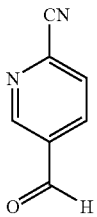

Method a):

Prepared in analogy to the procedure of Dodd, D. et al. [*J. Org. Chem.* 1992, 57, 7226-7234]: To a stirred solution of 5-(1,3-dioxolan-2-yl)-2-pyridinecarbonitrile (Example 2A; 850 mg, 4.8 mmol) in acetone/water 85:15 (59.5 ml) is given p-toluenesulphonic acid (102 mg, 0.59 mmol). The reaction is stirred it reflux overnight (18 h), then additional p-toluenesulphonic acid (50 mg) and water (5 ml) are added. The reaction is stirred at reflux for an additional 48 h. The solution is cooled to room temperature and quenched with saturated sodium bicarbonate solution. The product is extracted with ethyl acetate (3×100 ml), dried over magnesium sulphate monohydrate, filtered and concentrated in vacuo. The crude product is purified by preparative HPLC to afford a pale yellow solid.

Yield: 0.66 g (93% of th.)
Mp.: 80-82° C.
HPLC (method 4): 2.13 min.
MS (ESIpos): m/z=133 (M+H)⁺
¹H-NMR (400 MHz, DMSO-d₆): δ=10.18 (s, 1H), 9.21 (m, 1H), 8.49 (m, 1H), 8.27 (m, 1H) ppm.

Method b):

1.04 g (8.2 mmol) oxalylchloride are dissolved in 8 ml dichloromethane. At −78° C., 1.28 g (16.4 mmol) dimethylsulfoxide are added dropwise. The solution is stirred at −78° C. for 20 minutes, then 1 g (7.46 mmol) of the compound of Example 5A, dissolved in 7 ml dichloromethane, is added, and stirring at −78° C. is continued for another 2 hours. 3.4 g (33.6 mmol) triethylamine are then added dropwise, and after warming up to room temperature, the mixture is purified by column chromatography (silica, eluent cyclohexane to cyclohexane/ethyl acetate 2:1).

Yield: 0.76 g (77% of th.)
Analytical data: see above.

Example 4A

5-Methyl-2-pyridinecarbonitrile

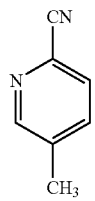

36 g (209 mmol) 2-bromo-5-methylpyridine and 37.5 g (418 mmol) copper cyanide are refluxed for two hours in 500 ml dimethylformamide. After cooling down to 50° C., 10% aqueous ammonia solution (500 ml) is added with stifling. The product is extracted with dichloromethane, the organic phase is dried over magnesium sulfate, and the solvent is removed in vacuo. The product is purified by column chromatography (silica, eluent cyclohexane/ethyl acetate 9:1):

Yield: 18 g (73% of th.)
¹H-NMR (300 MHz, CDCl₃): δ=2.4 (s, 3H), 7.6 (m, 2H), 8.6 (s, 1H) ppm.

Example 5A 5-(Hydroxymethyl)-2-pyridinecarbonitrile

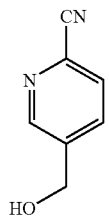

The compound of Example 4A (13 g, 110 mmol) is dissolved in 400 ml tetrachloro-methane, and 29.4 g (165 mmol) N-bromosuccinimide and 0.4 g (1.6 mmol) dibenzoylperoxide are added. The reaction mixture is refluxed for three hours, cooled down to room temperature and filtered. The solution is washed with aqueous sodium thiosulfate, dried over magnesium sulfate, and the solvent is removed in vacuo. The residue is dissolved in 200 ml dioxane and 200 ml water, calciumcarbonate (44 g, 440 mmol) is added, and the mixture is stirred at reflux for 2 hours. After cooling down to room temperature, the mixture is filtered, and dichloromethane is added. After phase separation, the organic phase is dried over magnesium sulfate, and the solvent is removed in vacuo. The product is purified by chromatography (silica, eluent cyclohexane/ethyl acetate 2:1).

Yield: 5.2 g (35% of th.)

$^1$H-NMR (300 MHz, DMSO-d$_6$): δ=4.7 (d, 2H), 5.6 (t, 1H), 8.0 (m, 2H), 8.7 (s, 1H) ppm.

PREPARATION EXAMPLES

Example 1

Ethyl 4-(4-cyanophenyl)-6-methyl-2-oxo-1-[3-(trifluoromethyl)phenyl]-1,2,3,4-tetra-hydro-5-pyrimidinecarboxylate

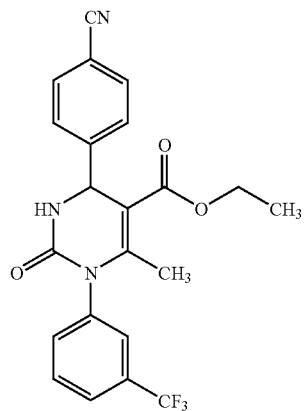

7.0 g (34.29 mmol) N-[3-(trifluoromethyl)phenyl]urea, 8.99 g (68.58 mmol) 4-cyanobenzaldehyde, 8.92 g (68.58 mmol) ethyl 3-oxobutanoate and 20 g poly-phosphoric acid ethyl ester are suspended in 250 ml of THF. The mixture is stirred at reflux for 18 hours. After cooling down to room temperature, the solvent is removed in vacuo and the residue is purified by column chromatography on silica with cyclohexane/ethyl acetate as eluent.

Yield: 13.4 g (91%)

$^1$H-NMR (200 Mz, DMSO-d$_6$): δ=1.1 (t, 3H); 2.0 (s, 3H); 4.0 (q, 2H); 5.4 (d, 1H); 7.6 (m, 3H); 7.7 (m, 3H); 7.9 (m, 2H); 8.4 (d, 1H) ppm.

Example 2

4-{5-Acetyl-6-methyl-2-oxo-1-[3-(trifluoromethyl)phenyl]-1,2,3,4-tetrahydro-4-pyrimidinyl}benzonitrile

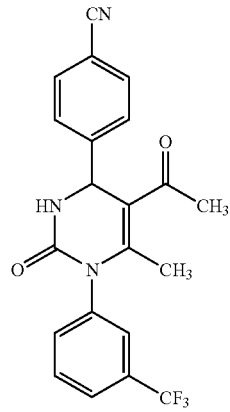

265 mg (1.3 mmol) N-[3-(trifluoromethyl)phenyl]urea, 131 mg (1.0 mmol) 4-cyano-benzaldehyde, and 100 mg (1.0 mmol) 2,4-pentanedione are suspended in 2 ml of THF, and catalytic amounts of concentrated hydrochloric acid are added. The mixture is stirred at reflux for 18 hours. After cooling down to room temperature, the solvent is removed in vacuo and the residue is purified by column chromatography on silica with cyclohexane/ethyl acetate as eluent.

Yield: 29 mg (7%)

$^1$H-NMR (200 MHz, DMSO-d$_6$): δ=2.0 (s, 3H); 2.2 (s, 3H); 5.5 (d, 1H); 7.5 (m, 1H); 7.6 (m, 3H); 7.7 (m, 1H); 7.8 (m, 1), 7.9 (m, 2H); 8.5 (d, 1H) ppm.

Example 3

Ethyl 4-(4-bromophenyl)-6-methyl-2-oxo-1-[3-(trifluoromethyl)phenyl]-1,2,3,4-tetrahydro-5-pyrimidinecarboxylate

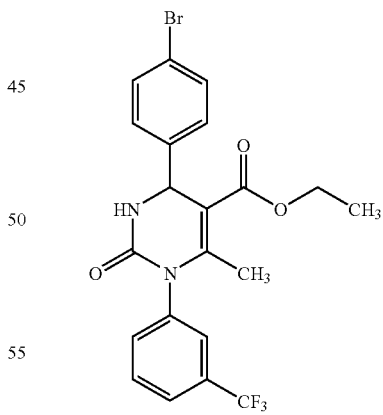

204 mg (1.0 mmol) N-[3-(trifluoromethyl)phenyl]urea, 142 mg (0.77 mmol) 4-bromobenzaldehyde, and 100 mg (0.77 mmol) ethyl 3-oxobutanoate are suspended in 2 ml of THF, and catalytic amounts of concentrated hydrochloric acid are added. The mixture is stirred at reflux for 18 hours. After cooling down to room temperature, the solvent is removed in vacuo and the residue is purified by column chromatography on silica with cyclohexane/ethyl acetate as eluent.

Yield: 23 mg (6%)

$^1$H-NMR (200 MHz, DMSO-$d_6$): δ=1.1 (t, 3H); 2.0 (s, 3H); 4.0 (q, 2H); 5.3 (d, 1H); 7.4 (m, 2H); 7.6 (m, 3H); 7.7 (m. 3H); 8.3 (d, 1H) ppm.

Example 4

Ethyl 4-(4-cyanophenyl)-6-methyl-2-oxo-1-[4-fluorophenyl]-1,2,3,4-tetrahydro-5-pyrimidinecarboxylate

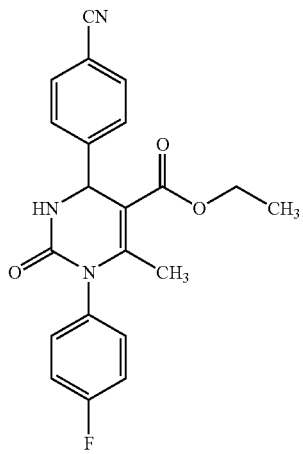

154 mg (1.0 mmol) N-[4-fluorophenyl]urea, 101 mg (0.77 mmol) 4-cyanobenzaldehyde, and 100 mg (0.77 mmol) ethyl 3-oxobutanoate are suspended in 2 ml of THF, and catalytic amounts of concentrated hydrochloric acid are added. The mixture is stirred at reflux for 18 hours. After cooling down to room temperature, the solvent is removed in vacuo and the residue is purified by column chromatography on silica with cyclohexane/ethyl acetate as eluent.

Yield: 40 mg (14%)

$^1$H-NMR (200 MHz, DMSO-$d_6$): δ1.1=(t, 3H); 2.0 (s, 3H); 4.0 (q, 2H); 5.3 (d, 1H); 7.3 (m, 4H); 7.5 (m, 2H); 7.9 (m, 2H); 8.3 (d, 1H) ppm.

Example 5

Ethyl 4-(4-cyanophenyl)-6-methyl-2-oxo-1-[3-chlorophenyl]-1,2,3,4-tetrahydro-5-pyrimidinecarboxylate

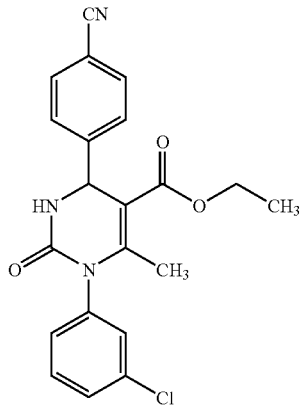

170 mg (1.0 mmol) N-[3-chlorophenyl]urea, 100 mg (0.77 mmol) 4-cyanobenzaldehyde and 100 mg (0.77 mmol) ethyl 3-oxobutanoate are suspended in 2 ml of THF, and catalytic amounts of concentrated hydrochloric acid are added. The mixture is stirred at reflux for 18 hours. After cooling down to room temperature, the solvent is removed in vacuo and the residue is purified by column chromatography on silica with cyclohexane/ethyl acetate as eluent.

Yield: 13 mg (4%)

$^1$H-NMR (200 MHz, DMSO-$d_6$): δ=1.1 (t, 3H); 2.1 (s, 3H); 4.0 (q, 2H); 5.3 (d, 1H); 7.2 (m, 1H); 7.4 (m, 3H); 7.5 (m, 2H); 7.9 (m, 2H); 8.3 (d, 1H) ppm.

Example 6

(1S)-2-Methoxy-1-methyl-2-oxoethyl 4-(4-cyanophenyl)-6-methyl-2-oxo-1-[3-(tri-fluoromethyl)phenyl]-1,2,3,4-tetrahydro-5-pyrimidinecarboxylate

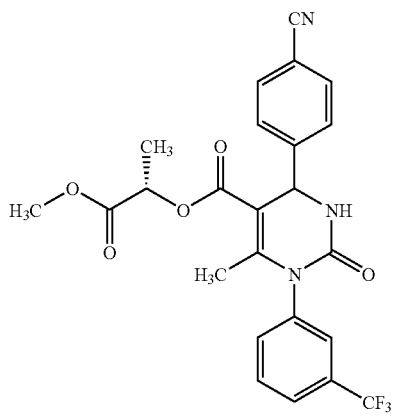

200 mg (0.98 mmol) N-[3-(trifluoromethyl)phenyl]urea, 129 mg (0.98 mmol) 4-cyanobenzaldehyde, 92 mg (0.49 mmol) (1S)-2-methoxy-1-methyl-2-oxoethyl 3-oxobutanoate, and 295 mg polyphosphoric acid ethyl ester are suspended in 3 ml of THF. The mixture is stirred at reflux for 18 hours. After cooling down to room temperature, the solvent is removed in vacuo and the residue is purified by column chromatography on silica with cyclohexane/ethyl acetate as eluent. A mixture of diastereoisomers is obtained.

Yield: 96 mg (40%)

$^1$H-NMR (200 MHz, DMSO-$d_6$): δ=1.3 (d, 3H); 1.4 (d, 3H); 2.0 (s, 3H+3H); 3.6 (s, 3H); 3.6 (s, 3H); 5.0 (m, 1H+1H); 5.4 (m, 1H+1H); 7.6-7.9 (m, 8H+8H); 8.4 (m, 1H+1H) ppm.

Example 7

4-{6-Methyl-5-(4-morpholinylcarbonyl)-2-oxo-1-[3-(trifluoromethyl)phenyl]-1,2,3,4-tetrahydro-4-pyrimidinyl}benzonitrile

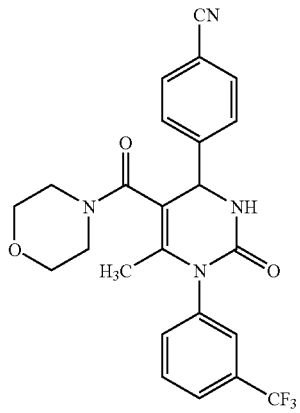

150 mg (0.73 mmol) N-[3-(trifluoromethyl)phenyl]urea, 96 mg (0.73 mmol) 4-cyanobenzaldehyde, 63 mg (0.37 mmol) 4-(4-morpholinyl)-4-oxo-2-butanone and 220 mg polyphosphoric acid ethyl ester are suspended in 3 ml of THF. The mixture is stirred at reflux for 18 hours. After cooling down to room temperature, the solvent is removed in vacuo and the residue is purified by column chromatography on silica with dichloromethane/methanol as eluent.

Yield: 28 mg (16%)

$^1$H-NMR (300 MHz, DMSO-$d_6$): δ=1.5 (s, 3H); 3.1 (m, 4H); 3.6 (m, 4H); 5.3 (br.s, 1H); 7.6 (m, 2H); 7.7 (m, 1H); 7.8 (m, 2H); 7.9 (m, 2H); 8.0 (br.s, 1H) ppm.

Example 8

4-(4-Cyanophenyl)-N,N-diethyl-6-methyl-2-oxo-1-[3-(trifluoromethyl)phenyl]-1,2,3,4-tetrahydro-5-pyrimidinecarboxamide

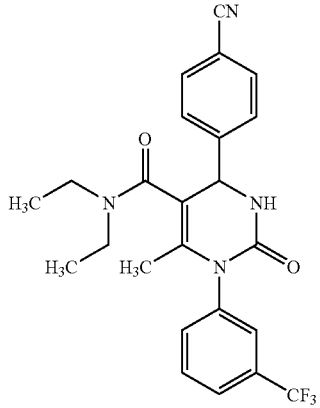

200 mg (0.98 mmol) N-[3-(trifluoromethyl)phenyl]urea, 128 mg (0.98 mmol) 4-cyanobenzaldehyde, 77 mg (0.49 mmol) 4-(4-diethylamino)-4-oxo-2-butanone and 295 mg polyphosphoric acid ethyl ester are suspended in 3 ml of THF. The mixture is stirred at reflux for 18 hours. After cooling down to room temperature, the solvent is removed in vacuo and the residue is purified by column chromatography on silica with dichloromethane/methanol as eluent.

Yield: 106 mg (47%)

$^1$H-NMR (300 MHz, DMSO-$d_6$): δ=0.9 (m, 6H); 3.1 (m, 4H); 5.2 (br.s, 1H); 7.6 (m, 2H); 7.7 (m, 1H); 7.8 (m, 2H); 7.9 (m, 2H); 8.0 (brs, 1H) ppm.

Example 9

6-Amino-4-(4-cyanophenyl)-2-oxo-1-[3-(trifluoromethyl)phenyl]-1,2,3,4-tetrahydro-5-pyrimidinecarbonitrile

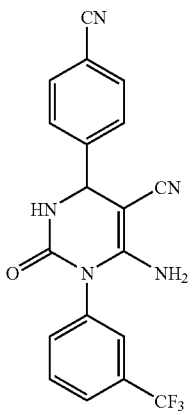

400 mg (1.97 mmol) N-[3-(trifluoromethyl)phenyl]urea, 199 mg (1.51 mmol) 4-cyanobenzaldehyde and 100 mg (1.51 mmol) malononitrile are suspended in 2 ml of THF, and catalytic amounts of concentrated hydrochloric acid are added. The mixture is stirred at reflux for 18 hours. After cooling down to room temperature, the solvent is removed in vacuo and the residue is purified by column chromatography on silica with dichloromethane/methanol as eluent.

Yield: 4 mg (1%)

$^1$H-NMR. (400 MHz, DMSO-$d_6$): δ=5.2 (d, 1H); 6.0 (s, 2H); 7.6 (m, 3H); 7.7 (m, 2H); 7.8 (m, 1H); 7.9 (m, 2H) 8.4 (d, 1H) ppm.

Example 10

Ethyl 4-(4-cyanophenyl)-3-formyl-6-methyl-2-oxo-1-[3-(trifluoromethyl)phenyl]-1,2,3,4-tetrahydro-5-pyrimidinecarboxylate

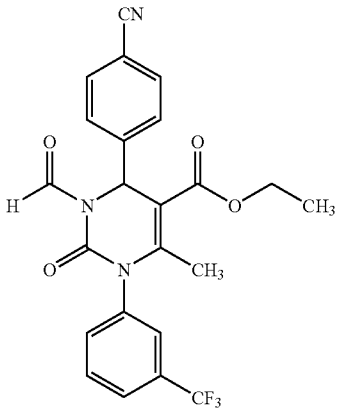

100 mg (0.23 mmol) of Example 1 are dissolved in 1 ml dimethylformamide, and 35.7 mg (0.23 mmol) phosphorylchloride are added. The reaction mixture is stirred at 70° C. for two hours. After cooling down to room temperature, the product is isolated by preparative HPLC.

Yield: 43 mg (41%)

$^1$H-NMR (300 MHz, DMSO-$d_6$): δ=1.1 (t, 3H); 2.1 (s, 3H); 4.1 (q, 2H); 6.4 (s, 1H); 7.6 (m, 2H); 7.7 (m, 1H); 7.8 (m, 1H); 7.9 (m, 4H); 9.2 (s, 1H) ppm.

Example 11

4-(4-Cyanophenyl)-6-methyl-2-oxo-1-[3-(trifluoromethyl)phenyl]-1,2,3,4-tetrahydro-5-pyrimidinecarboxylic acid

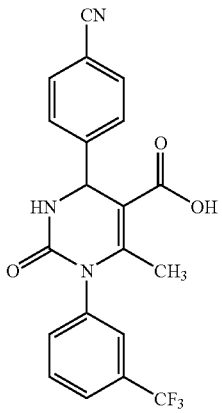

3 g (7 mmol) of Example 1 are dissolved in a mixture of 50 ml water and 100 ml 5% KOH in ethanol. The reaction mixture is stirred at room temperature for 18 hours. The solvent is removed in vacuo and the residue is purified by column chromatography on silica with dichloromethane/methanol as eluent.

Yield: 1.27 g (45%)

$^1$H-NMR (300 MHz, DMSO-$d_4$): δ=2.0 (s, 3H); 5.4 (d, 1H); 7.6 (m, 1H); 7.6 (m, 2H); 7.7 (m, 1H); 7.8 (m, 1H); 7.9 (m, 3H); 8.3 (d, 1H); 12.5 (s, 1H) ppm.

Example 12

4-(4-Cyanophenyl)-6-methyl-2-oxo-N-propyl-1-[3-(trifluoromethyl)phenyl]-1,2,3,4-tetrahydro-5-pyrimidinecarboxamide

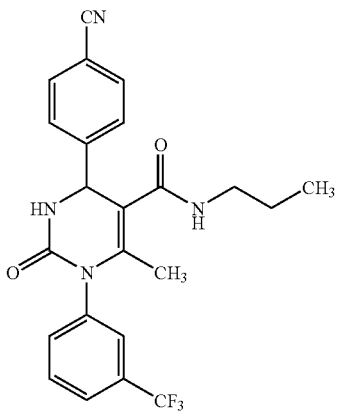

40 mg (0.1 mmol) of Example 11 are dissolved in 2 ml dimethylformamide, 7 mg (0.11 mmol) n-propylamine, 15 mg (0.11 mmol) 1-hydroxy-1H-benzotriazole hydrate and 12 mg (0.1 mmol) 4-dimethylaminopyridine are added. The reaction mixture is stirred at 0° C., then 21 mg (0.11 mmol) 1-(3-dimethylaminopropyl)-3-ethylcarbodiimide hydrochloride are added. The reaction mixture is stirred at room temperature for 18 hours, then water and ethyl acetate are added. The organic phase is washed with saturated aqueous KHSO$_4$, water and brine, dried over sodium sulfate and evaporated to dryness in vacuo. If necessary, the product is further purified by column chromatography or preparative HPLC.

Yield: 29 mg (66%)

$^1$H-NMR (300 MHz, DMSO-$d_6$): δ=0.7 (t, 3H); 1.3 (sext, 2H); 1.7 (s, 3H); 3.0 (q, 2H); 5.4 (d, 1H); 7.6 (m, 3H); 7.7 (m, 2H); 7.8 (m, 2H); 7.9 (m, 1H); 8.1 (d, 1H) ppm.

Example 13

4-(4-Cyanophenyl)-N-(2-methoxyethyl)-6-methyl-2-oxo-1-[3-(trifluoromethyl)-phenyl]-1,2,3,4-tetrahydro-5-pyrimidinecarboxamide

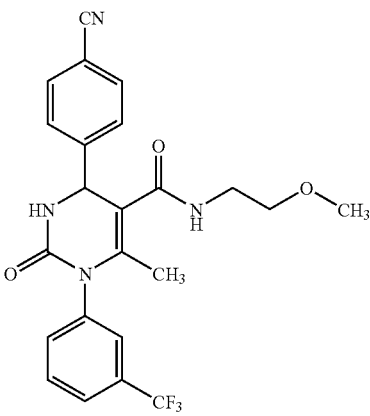

48 mg (0.12 mmol) of Example 11 are dissolved in 2 ml dimethylformamide, 10 mg (0.13 mmol) 2-methoxyethylamine, 18 mg (0.13 mmol) 1-hydroxy-1H-benzotriazole hydrate and 15 mg (0.12 mmol) 4-dimethylaminopyridine are added. The reaction mixture is stirred at 0° C., then 25 mg (0.13 mmol) 1-(3-dimethylaminopropyl)-3-ethylcarbodiimide hydrochloride are added. The reaction mixture is stirred at room temperature for 18 hours, then water and ethyl acetate are added. The organic phase is washed with saturated aqueous KHSO$_4$, water and brine, dried over sodium sulfate and evaporated to dryness in vacuo. If necessary, the product is further purified by column chromatography or preparative HPLC.

Yield: 22 mg (40%)

$^1$H-NMR (300 MHz, DMSO-$d_6$): δ=1.7 (s, 3H); 3.2 (s, 3H); 3.3 (m, 4H); 5.4 (d, 1H); 7.6 (m, 3H); 7.7 (m, 3H); 7.9 (m, 2H); 8.1 (m, 1H) ppm.

Example 14

Ethyl 4-(4-cyanophenyl)-3,6-dimethyl-2-oxo-1-[3-(trifluoromethyl)phenyl]-1,2,3,4-tetrahydro-5-pyrimidinecarboxylate

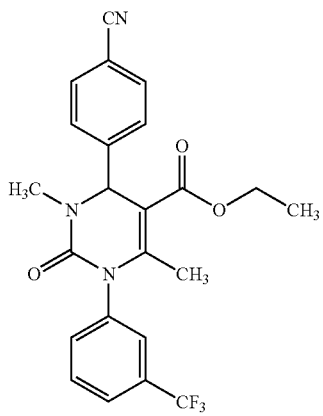

89 mg (0.21 mmol) of Example 1 are added to a suspension of 12.4 mg (0.31 mmol) 60% sodium hydride (in mineral oil) in 2 ml THF. The mixture is stirred at room temperature for two hours. Then 26 mg (0.21 mmol) dimethylsulfate are added, and the mixture is stirred at room temperature for another 2 hours. Then water and ethyl acetate are added, and the organic phase is washed with water and brine, dried over sodium sulfate and evaporated to dryness in vacuo. If necessary, the product is further purified by column chromatography or preparative HPLC.

Yield: 85 mg (93%)

$^1$H-NMR (200 MHz, DMSO-$d_6$): δ=1.1 (t, 3H); 2.0 (s, 3H); 2.8 (s, 3H); 4.0 (q, 2H); 5.5 (s, 1H); 7.6 (m, 3H); 7.7 (m, 1H); 7.8 (m, 2H); 7.9 (m, 2H) ppm.

Example 15

Ethyl 3-acetyl-4-(4-cyanophenyl)-6-methyl-2-oxo-1-[3-(trifluoromethyl)phenyl]-1,2,3,4-tetrahydro-5-pyrimidinecarboxylate

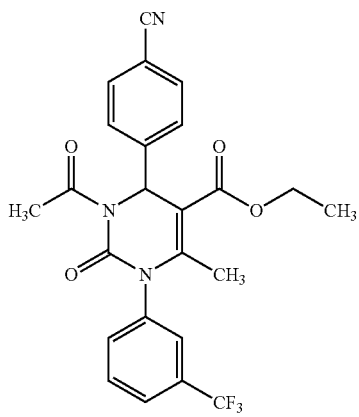

100 mg (0.23 mmol) of Example 1 are added to a suspension of 12 mg (0.28 mmol) 60% sodium hydride (in mineral oil) in 2 ml THF. The mixture is stirred at room temperature for two hours. Then 91 mg (1.16 mmol) acetylchloride are added, and the mixture is stirred at room temperature for another 2 hours. Then water and ethyl acetate are added, and the organic phase is washed with water and brine, dried over sodium sulfate and evaporated to dryness in vacuo. If necessary, the product is further purified by column chromatography or preparative HPLC.

Yield: 93 mg (85%)

$^1$H-NMR (200 MHz, DMSO-$d_6$): δ=1.2 (t, 3H); 2.1 (s, 3H); 2.5 (s, 3H); 4.2 (m, 2H) 6.7 (s, 1H); 7.4 (m, 1H); 7.5 (m, 2H); 7.6 (m, 1H); 7.7 (m, 1H); 7.8 (m, 1H); 7.9 (m, 2H) ppm.

Example 16

Diethyl 6-(4-cyanophenyl)-4-methyl-2-oxo-3-[3-(trifluoromethyl)phenyl]-3,6-di-hydro-1,5(2H)-pyrimidinedicarboxylate

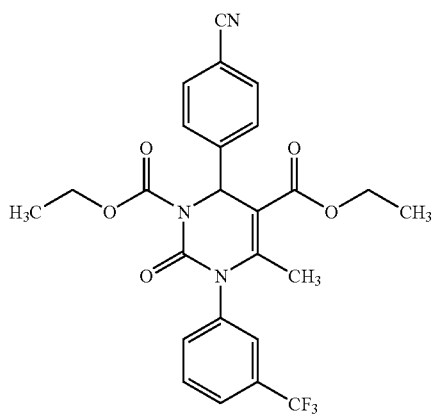

100 mg (0.23 mmol) of Example 1 are added to a suspension of 12 mg (0.28 mmol) 60% sodium hydride (in mineral oil) in 2 ml THF. The mixture is stirred at room temperature for two hours. Then 126 mg (1.16 mmol) ethyl chloridocarbonate are added, and the mixture is stirred at room temperature for another 2 hours. Then water and ethyl acetate are added, and the organic phase is washed with water and brine, dried over sodium sulfate and evaporated to dryness in vacuo. If necessary, the product is further purified by column chromatography or preparative HPLC.

Yield: 92 mg (79%)

$^1$H-NMR (200 MHz, DMSO-$d_6$): δ=1.2 (t, 3H; t, 3H); 2.1 (s, 3H); 4.2 (m, 2H); 4.3 (q, 2H); 6.4 (s, 1H); 7.4 (m, 1H); 7.5 (m, 3H); 7.7 (m, 1H); 7.8 (m, 1H); 7.9 (m, 2H) ppm.

Example 17

Ethyl 4-(4-cyanophenyl)-6-methyl-1-(3-methylphenyl)-2-oxo-1,2,3,4-tetrahydro-5-pyrimidinecarboxylate

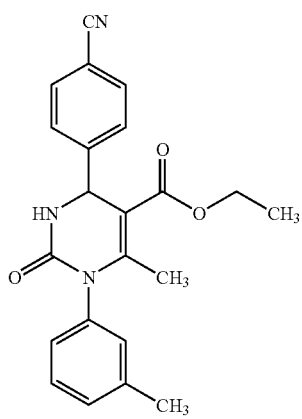

150 mg (1.0 mmol) N-[3-methylphenyl]urea, 101 mg (0.77 mmol) 4-cyanobenzaldehyde and 100 mg (0.77 mmol) ethyl 3-oxobutanoate are suspended in 2 ml of THF, and catalytic amounts of concentrated hydrochloric acid are added. The mixture is stirred at reflux for 18 hours. After cooling down to room temperature, the solvent is removed in vacuo and the residue is purified by column chromatography on silica with cyclohexane/ethyl acetate as eluent.

Yield: 8 mg (3%)

$^1$H-NMR (200 MHz, DMSO-$d_6$): δ=1.1 (t, 3H); 2.0 (s, 3H); 2.3 (s, 3H); 4.0 (q, 2H); 5.3 (d, 1H); 7.0 (m, 2H); 7.2 (m, 1H); 7.3 (m, 1H); 7.6 (m, 2H); 7.9 (m, 2H); 8.2 (d, 1H) ppm.

Example 18

Ethyl 4-(4-chlorophenyl)-6-methyl-2-oxo-1-[3-(trifluoromethyl)phenyl]-1,2,3,4-tetrahydro-5-pyrimidinecarboxylate

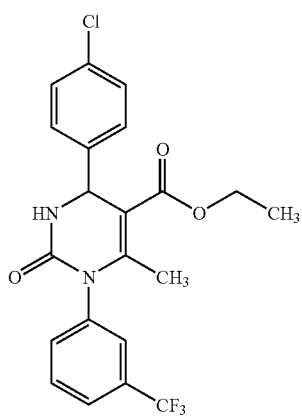

204 mg (1.0 mmol) N-[3-(trifluoromethyl)phenyl]urea, 108 mg (0.77 mmol) 4-chlorobenzaldehyde and 100 mg (0.77 mmol) ethyl 3-oxobutanoate are suspended in 2 ml of THF, and catalytic amounts of concentrated hydrochloric acid are added. The mixture is stirred at reflux for 18 hours. After cooling down to room temperature, the solvent is removed in vacuo and the residue is purified by column chromatography on silica with cyclohexane/ethyl acetate as eluent.

Yield: 29 mg (9%)

$^1$H-NMR (200 MHz, DMSO-$d_6$): δ=1.1 (t, 3H); 2.0 (s, 3H); 4.0 (q, 2H); 5.3 (d, 1H); 7.5 (m, 5H); 7.6 (m, 1H); 7.7 (m, 2H); 8.3 (d, 1H) ppm.

Example 19

Ethyl 6-(bromomethyl)-4-(4-cyanophenyl)-2-oxo-1-[3-trifluoromethyl)phenyl]-1,2,3,4-tetrahydro-5-pyrimidinecarboxylate

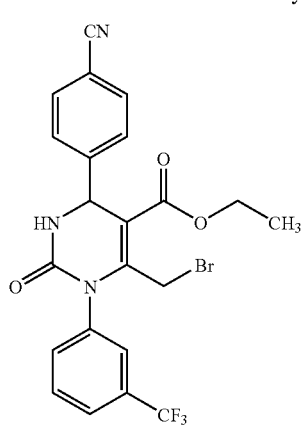

3 g (7 mmol) of Example 1 are dissolved in 100 ml chloroform. At 0° C., 558 mg (3.48 mmol) bromine are added dropwise. The mixture is stirred at room temperature for two hours, then the solvent is removed in vacuo. The residue is purified by column chromatography on silica with cyclohexane/ethyl acetate as eluent.

Yield: 3.2 g (90%)

$^1$H-NMR (200 MHz, DMSO-$d_6$): δ=1.1 (t, 3H); 4.0 (q, 2H, d, 1H); 4.6 (br d, 1H); 5.4 (d, 1H); 7.6 (m, 3H); 7.7 (m, 2H); 7.8 (m, 1H); 7.9 (m, 2H); 8.6 (d, 1H) ppm.

Example 20

Ethyl 4-(4-cyanophenyl)-6-[(diethylamino)methyl]-2-oxo-1-[3-(trifluoromethyl)-phenyl]-1,2,3,4-tetrahydro-5-pyrimidinecarboxylate

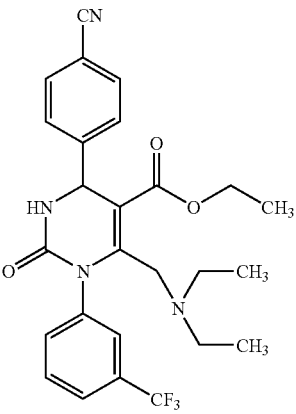

20 mg (0.04 mmol) of Example 19 are dissolved in 2 ml acetone, and 8 mg (0.10 mmol) diethylamine are added The mixture is stirred at room temperature for 18 hours, then the solvent is removed in vacuo. The residue is purified by preparative HPLC.

Yield: 15 mg (75%)

$^{1}$H-NMR (300 MHz, DMSO-$d_6$): δ=0.6 (t, 6H); 1.1 (t, 3H); 2.0 (m, 2H); 2.2 (m, 2H); 3.1 (br d, 1H); 3.9 (br d, 1H); 4.1 (q, 2H); 5.4 (d, 1H); 7.5 (m, 1H); 7.6 (m, 4H); 7.7 (m, 1H); 7.9 (m, 2H) ppm.

Example 21

Ethyl 6-(anilinomethyl)-4-(4-cyanophenyl)-2-oxo-1-[3-(trifluoromethyl)phenyl]-1,2,3,4-tetrahydro-5-pyrimidinecarboxylate

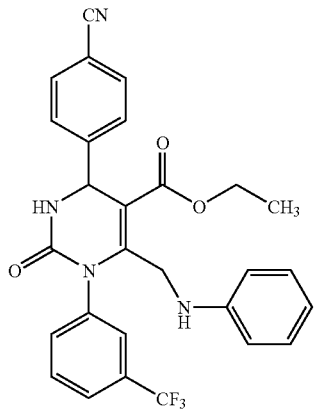

50 mg (0.10 mmol) of Example 19 are dissolved in 2 ml acetone, and 18 mg (0.20 mmol) aniline are added. The mixture is stirred at room temperature for 18 hours, then the solvent is removed in vacuo. The residue is purified by preparative HPLC.

Yield: 28 mg (55%)

$^{1}$H-NMR (300 MHz, DMSO-$d_6$): δ=1.1 (t, 3H); 3.6 (d/d, 1H); 4.1 (q, 2H); 4.4 (d/d, 1H); 5.4 (m, 2H); 6.2 (m, 2H); 6.5 (m, 1H); 6.9 (m, 2H); 7.6 (m, 6H); 7.9 (m, 2H); 8.4 (d, 1H) ppm.

Example 22

(+)-Ethyl 4-(4-cyanophenyl)-6-methyl-2-oxo-1-[3-(trifluoromethyl)phenyl]-1,2,3,4-tetrahydro-5-pyrimidinecarboxylate

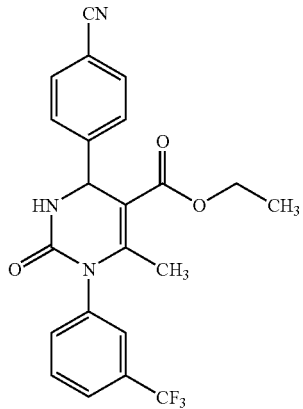

The enantiomers of Example 1 are separated by preparative HPLC on a chiral phase: 100 mg compound dissolved in 1.5 ml ethyl acetate, column KBD 8361 (chiral silica gel selector based on monomer N-methacryloyl-L-leucine-1-menthylamide, cf. EP-A-379 917), 250 mm×20 mm, eluent ethyl acetate, flow 25 ml/min, temperature 23° C., injection volume 2500 μl, detection 254 nm.

$^{1}$H-NMR (300 MHz, DMSO-$d_6$): δ=1.1 (t, 3H); 2.0 (s, 3H); 4.0 (q, 2H); 5.4 (d, 1H); 7.6 (m, 3H); 7.7 (m, 2H); 7.8 (m, 1H); 7.9 (m, 2H); 8.4 (d, 1H) ppm.

$[α]^{20}$-+3.3° (λ=589 nm, dichloromethane, c=535.0 mg/100 ml)

Example 23

(−)-Ethyl 4-(4-cyanophenyl)-3,6-dimethyl-2-oxo-1-[3-(trifluoromethyl)phenyl]-1,2,3,4-tetrahydro-5-pyrimidinecarboxylate

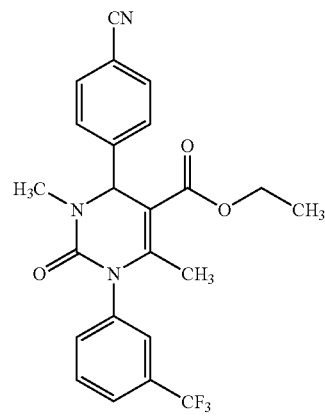

100 mg (0.23 mmol) of Example 22 are added to a suspension of 14 mg (0.35 mmol) 60% sodium hydride (in mineral oil) in 2 ml THF. The mixture is stirred at room temperature for two hours. Then 29 mg (0.23 mmol) dimethylsulfate are added, and the mixture is stirred at room temperature for another 2 hours. Then water and ethyl acetate are added, the organic phase is washed with water and brine, dried over sodium sulfate and evaporated to dryness in vacuo. The product is purified by column chromatography on silica with cyclohexane/ethyl acetate as eluent.

Yield: 76 mg (74%)

$^{1}$H-NMR (200 MHz, DMSO-$d_6$): δ=1.1 (t, 3H); 2.0 (s, 3H); 2.8 (s, 3H); 4.0 (q, 2H); 5.5 (s, 1H); 7.6 (m, 3H); 7.7 (m, 1H); 7.8 (m, 2H); 7.9 (m, 2H) ppm.

$[α]^{20}$=−18.1° (λ=589 nm, dichloromethane, c=530.0 mg/100 ml)

Example 24

Ethyl 4-(6-cyano-3-pyridinyl)-6-methyl-2-oxo-1-[3-(trifluoromethyl)phenyl]-1,2,3,4-tetrahydro-5-pyrimidinecarboxylate

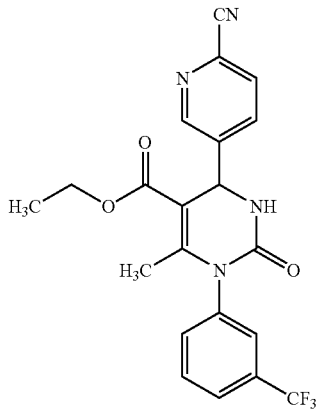

To a stirred solution of Example 3A (76 mg, 0.58 mmol) in tetrahydrofuran (5 ml) is given ethyl 3-oxobutanoate (75 mg, 0.58 mmol), N-[3-(trifluoromethyl)phenyl]urea (118 mg, 0.58 mmol) and polyphosphoric acid ethyl ester (200 mg; freshly prepared according to the procedure of Cava et al., J. Org. Chem. 1969, 34, 2665). The reaction mixture is refluxed for two days (48 hours) after which time the solution is diluted with DMSO (2 ml) and purified by preparative HPLC. The product fractions are concentrated in vacuo and chromatographed again over silica with cyclohexane and ethyl acetate as eluent.

Yield: 92 mg (35% of th.)

MS (ESIpos): m/z=431 (M+H)$^+$

HPLC (method-4)=4.63 min $^1$H-NMR (300 MHz, DMSO-d$_6$): δ=8.76 (s, 1H), 8.36 (d, 1H), 8.16-8.00 (m, 2H), 7.83-7.74 (m, 2H), 7.75-7.58 (m, 2H), 5.47 (d, 1H), 4.03 (quartet, 2H), 2.06 (s, 3H), 1.08 (t, 3H) ppm.

Example 25

4-{5-(1H-Imidazol-1-ylcarbonyl)-6-methyl-2-oxo-1-[3-(trifluoromethyl)phenyl]-1,2,3,4-tetrahydro-4-pyrimidinyl}benzonitrile

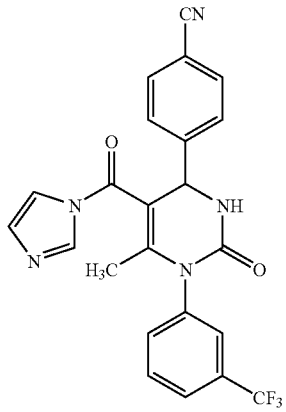

To a solution of 501 mg (1.25 mmol) of the compound of Example 11 in 5 ml dry dimethylformamide are added 567 mg (3.5 mmol) N,N-carbonyldiimidazole. After allowing the reaction mixture to stand overnight, the solvent is evaporated off in vacuo. The residue is taken up in ethyl acetate and washed with water and brine. After drying with magnesium sulfate the solvent is evaporated off in vacuo.

Yield: 500 mg (88.6% of th.)

MS (ET): m/z=452 (M+H)$^+$ $^1$H-NMR (200 MHz, DMSO-d$_6$): δ=1.40 (d, 3H), 5.5 (d, 1H), 7.0 (s, 1H), 7.55-8.0 (m, 9H), 8.4 (s, 1H), 8.45 (d, 1H) ppm.

Example 26

2-Hydroxyethyl 4-(4-cyanophenyl)-6-methyl-2-oxo-1-[3-(trifluoromethyl)phenyl]-1,2,3,4-tetrahydro-5-pyrimidinecarboxylate

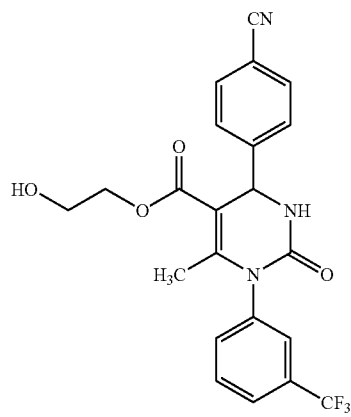

45.1 mg (0.1 mmol) of the compound of Example 25 are added to 0.5 ml ethylene glycol. The reaction mixture is stirred at approx. 100° C. for 1 hour. After cooling the reaction mixture is purified by preparative HPLC (column: Agilent Zorbax Extend C18 20 mm×50 mm, 5 µm; solvent A: acetonitrile, solvent B: water+0.1% conc. ammonia; gradient: 0 min 10% A, 2 min 10% A, 6 min 90% A, 7 min 90% A, 7.1 min 10% A, 8 min 10% A; wavelength: 220 nm; injection volume: approx. 500 µl; number of injections: 1). The product containing fractions are combined and concentrated in vacuo.

Yield: 22 mg (49.4% of th.)

MS (EI): m/z=446 (M+H)$^+$ $^1$H-NMR (300 MHz, DMSO-d$_6$): δ2.05 (d, 3H)-3.5 (quartet, 2H), 3.95-4.15 (m, 2H), 4.75 (tr, 1H), 5.45 (d, 1H), 7.55-7.75 (m, 5H), 7.75 (d, 1H), 7.85 (d, 2H), 8.35 (d, 1H) ppm.

Example 27

2-(Dimethylamino)ethyl 4-(4-cyanophenyl)-6-methyl-2-oxo-1-[3-(trifluoromethyl)-phenyl]-1,2,3,4-tetrahydro-5-pyrimidinecarboxylate

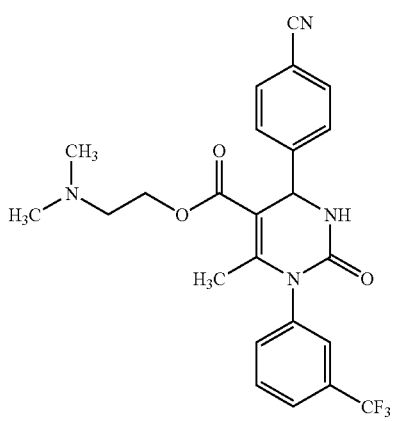

45.1 mg (0.1 mmol) of the compound of Example 25 are added to 0.5 ml 2-(dimethylamino)ethanol. The reaction mixture is stirred at approx. 100° C. for 1 hour. After cooling the reaction mixture is purified by preparative HPLC (column: Agilent Zorbax Extend C18 20 mm×50 mm, 5 µm; solvent A: acetonitrile, solvent B: water+0.1% conc. ammonia; gradient: 0 min 10% A, 2 min 10% A, 6 min 90% A, 7 min 90% A, 7.1 min 10% A, 8 min 10% A; wavelength: 220 nm; injection volume: approx. 500 µl; number of injections: 1). The product containing fractions are combined and concentrated in vacuo.

Yield: 24 mg (50.8% of th.)

MS (EI): m/z=473 (M+H)+

$^1$H-NMR (300 MHz, DMSO-d$_6$): δ=2.05 (d, 3H), 2.1 (s, 6H), 2.4 (m, 2H), 4.1 (m, 2H), 5.35 (d, 1H), 7.55 (d, 1H), 7.6 (d, 2H), 7.7 (m, 2H), 7.8 (d, 1H), 7.85 (d, 2H), 8.35 (d, 1H) ppm.

Example 28

2-(4-Pyridinyl)ethyl 4-(4-cyanophenyl)-6-methyl-2-oxo-1-[3-(trifluoromethyl)phenyl]-1,2,3,4-tetrahydro-5-pyrimidinecarboxylate

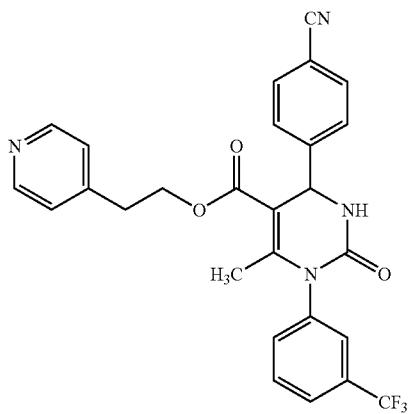

45.1 mg (0.1 mmol) of the compound of Example 25 are added to 0.5 ml 2-(4-pyridinyl)ethanol. The reaction mixture is stirred at approx. 100° C. for 1 hour. After cooling the reaction mixture is purified by preparative HPLC (column: Agilent Zorbax Extend C18 20 mm×50 mm, 5 µm; solvent A: acetonitrile, solvent B: water+0.1% conc. ammonia; gradient: 0 min 10% A, 2 min 10% A, 6 min 90% A, 7 min 90% A, 7.1 min 10% A, 8 min 10% A; wavelength: 220 nm; injection volume: approx. 500 µl; number of injections: 1). The product containing fractions are combined and concentrated in vacuo.

Yield: 17 mg (33.5% of th.)

MS (EI): m/z=507 (M+H)+

$^1$H-NMR (300 MHz, DMSO-d$_6$): δ=2.0 (d, 3H), 2.9 (tr, 21H), 4.3 (tr, 2H), 5.25 (d, 1H), 7.15 (d, 2H), 7.45 (d, 2H), 7.5 (d, 1H), 7.65 (tr, 2H), 7.8 (m, 3H), 8.35 (d, 1H), 8.4 (d, 2H) ppm.

Example 29

2-(2-Pyridinyl)ethyl 4-(4-cyanophenyl)-6-methyl-2-oxo-1-[3-(trifluoromethyl)phenyl]-1,2,3,4-tetrahydro-5-pyrimidinecarboxylate

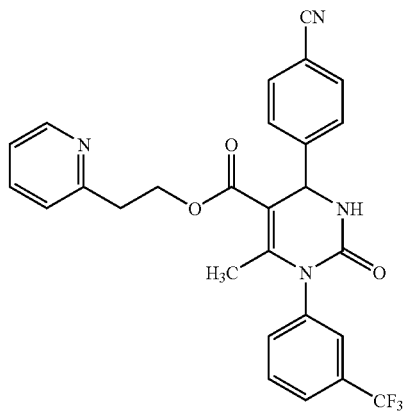

45.1 mg (0.1 mmol) of the compound of Example 25 are added to 0.5 ml 2-(2-pyridinyl)ethanol. The reaction mixture is stirred at approx. 100° C. for 1 hour. After cooling the reaction mixture is purified by preparative HPLC (column: Agilent Zorbax Extend C18 20 mm×50 mm, 5 µm; solvent A: acetonitrile, solvent B: water+0.1% conc. ammonia; gradient: 0 min 10% A, 2 min 10% A, 6 min 90% A, 7 min 90% A, 7.1 min 10% A, 8 min 10% A; wavelength: 220 nm; injection volume: approx. 500 µl; number of injections: 1). The product containing fractions are combined and concentrated in vacuo.

Yield: 22 mg (43.4% of th.)

MS (EI): m/z=507 (M+H)+

$^1$H-NMR (300 MHz, DMSO-d$_6$): δ=2.0 (d, 3H), 3.0 (tr, 2H), 4.4 (tr, 2H), 5.25 (d 1H), 7.15-7.25 (m, 2H), 7.4 (d, 2H), 7.5 (d, 1H), 7.6-7.75 (m, 3H), 7.8 (m, 3H), 8.3 (d, 1H), 8.45 (d, 1H) ppm.

Example 30

2-(2-Oxo-1-pyrrolidinyl)ethyl 4-(4-cyanophenyl)-6-methyl-2-oxo-1-[3-(trifluoro-methyl)phenyl]-1,2,3,4-tetrahydro-5-pyrimidinecarboxylate

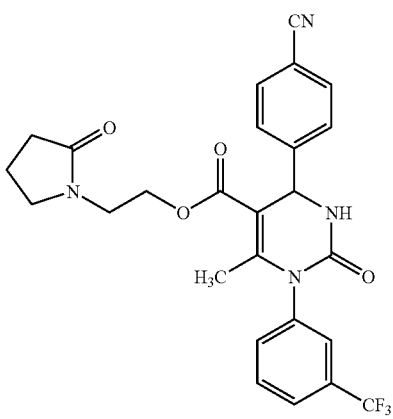

45.1 mg (0.1 mmol) of the compound of Example 25 are added to 0.5 ml 1-(2-hydroxyethyl)-2-pyrrolidinone. The reaction mixture is stirred at approx. 100° C. for 1 hour. After cooling the reaction mixture is purified by preparative HPLC (column: Agilent Zorbax Extend C18 20 mm×50 mm, 5 µm; solvent A: acetonitrile, solvent B: water+0.1% conc. ammonia; gradient: 0 min 10% A, 2 min 10% A, 6 min 90% A, 7 min 90% A, 7.1 min 10% A, 8 min 10% A; wavelength: 220 nm; injection volume: approx. 500 µl; number of injections: 1). The product containing fractions are combined and concentrated in vacuo.

Yield: 25 mg (48.8% of th.)

MS (EI): m/z=513 (M+H)$^+$ $^1$H-NMR (300 Mz, DMSO-d$_6$): δ=1.8 (quintet, 2H), 2.0 (d, 3H), 2.1 (tr, 2H), 3.2 (tr, 2H), 3.4 (tr, 2H), 4.0-4.2 (m, 2H), 5.35 (d, 1H), 7.55 (d, 1H), 7.6 (d, 2H), 7.7 (tr, 2H), 7.8 (d, 1H), 7.9 (d, 2H), 8.4 (d, 1H) ppm.

In analogy to the procedures for Examples 14-16, the following compounds are prepared:

| Example No. | Structure | Starting materials | Yield [%] | R$_t$ [min] (method) | Mass [M + H]$^+$ |
|---|---|---|---|---|---|
| 31 | 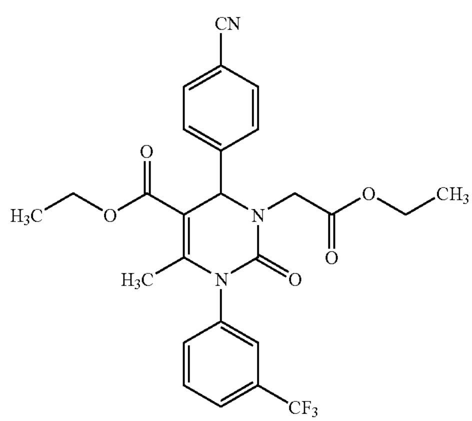 | Example 1; ethyl bromoacetate | 85 | 4.01 (1) | 516 |
| 32 | 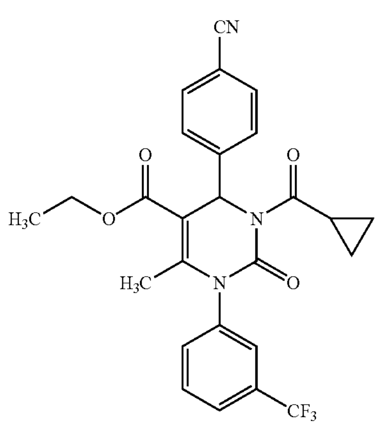 | Example 1; cyclopropane-carbonyl chloride | 79 | 4.09 (1) | 498 |

-continued

| Example No. | Structure | Starting materials | Yield [%] | R$_t$ [min] (method) | Mass [M + H]$^+$ |
|---|---|---|---|---|---|
| 33 | 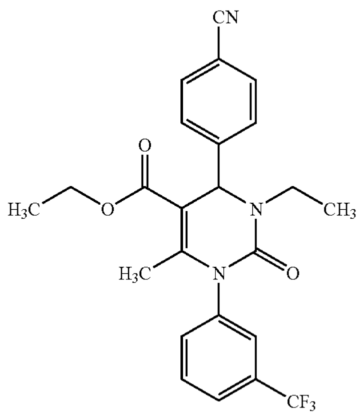 | Example 1; bromoethane | 15 | 4.28 (2) | 458 |
| 34 | 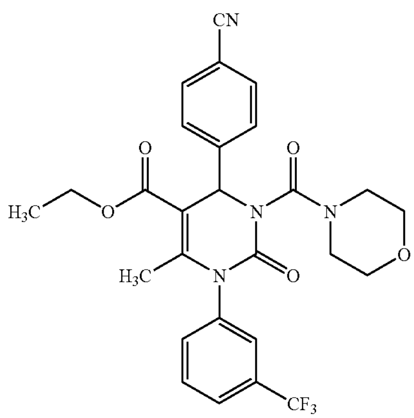 | Example 1; 4-morpholine-carbonyl chloride | 97 | 3.97 (2) | 543 |
| 35 | 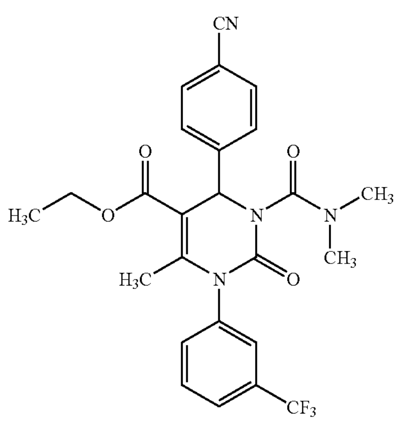 | Example 1; dimethyl-carbamic chloride | 98 | 4.00 (2) | 523 [M+Na]$^+$ |

-continued

| Example No. | Structure | Starting materials | Yield [%] | R$_t$ [min] (method) | Mass [M + H]$^+$ |
|---|---|---|---|---|---|
| 36 | 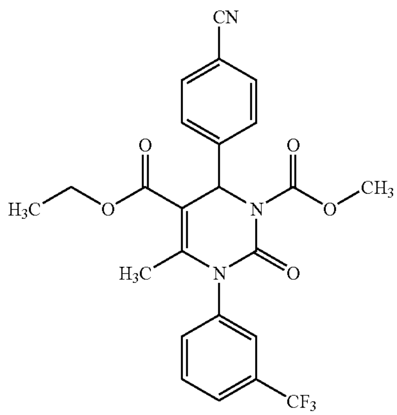 | Example 1; methyl chlorido-carbonate | 96 | 4.10 (2) | 488 |
| 37 | 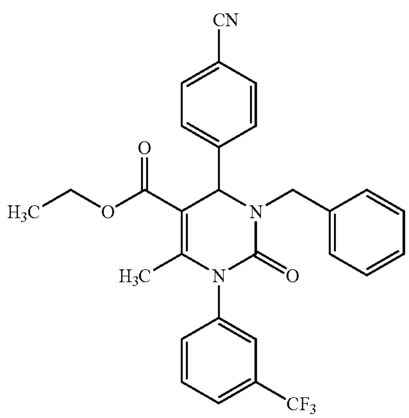 | Example 1; benzylbromide | 58 | 4.59 (2) | 520 |
| 38 | 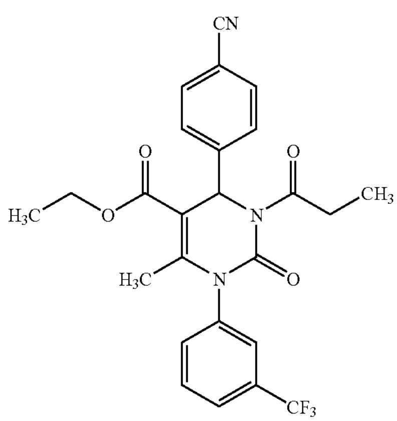 | Example 1; propanoyl chloride | 43 | 4.42 (2) | 486 |

-continued

| Example No. | Structure | Starting materials | Yield [%] | $R_t$ [min] (method) | Mass $[M + H]^+$ |
|---|---|---|---|---|---|
| 39 | 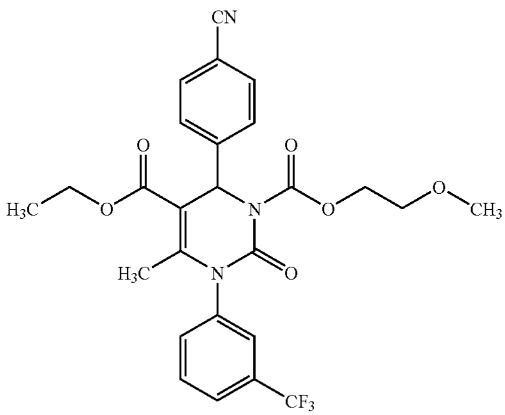 | Example 1; 2-methoxyethyl chlorido-carbonate | 95 | 4.12 (2) | 532 |
| 40 | 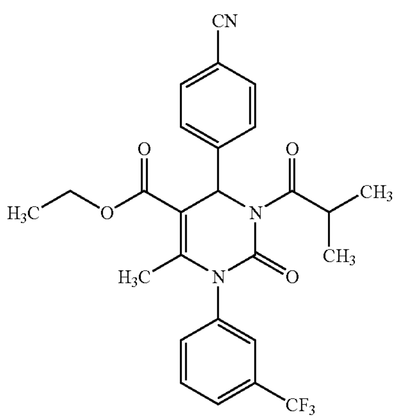 | Example 1; isopropyl chlorido-carbonate | 67 | 4.55 (2) | 500 |
| 41 | 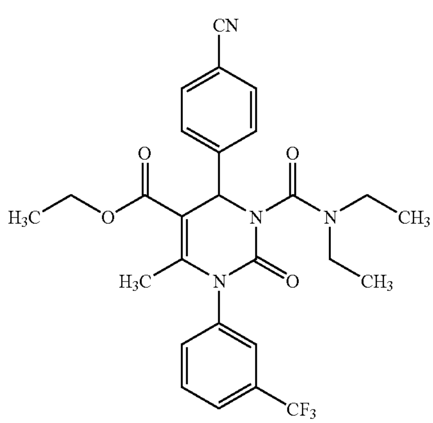 | Example 1; diethylcarbamic chloride | 18 | 4.25 (2) | 529 |

-continued

| Example No. | Structure | Starting materials | Yield [%] | $R_t$ [min] (method) | Mass [M + H]$^+$ |
|---|---|---|---|---|---|
| 42 | 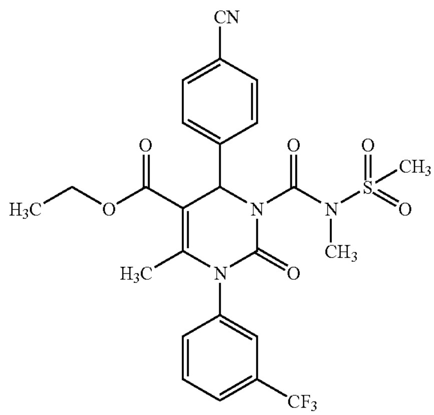 | Example 1; methyl (methyl-sulfonyl)-carbamic chloride | 40 | 4.10 (2) | 565 |
| 43 | 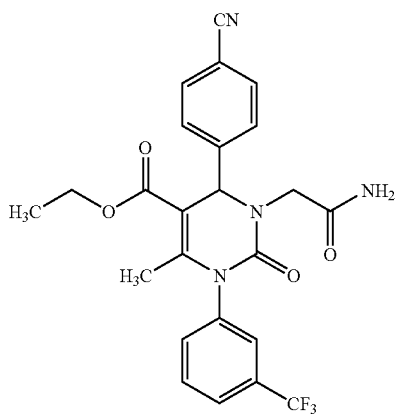 | Example 1; 2-bromo-acetamide; 2.5 equiv. NaH | 54 | 3.7 (3) | 487 |
| 44 | 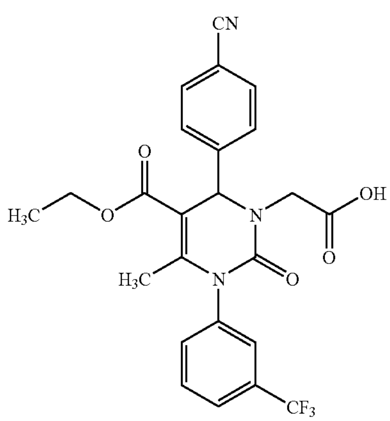 | Example 1; 2-bromoacetic acid; 2.5 equiv. NaH | 67 | 3.8 (3) | 488 |

-continued

| Example No. | Structure | Starting materials | Yield [%] | R_t [min] (method) | Mass [M + H]+ |
|---|---|---|---|---|---|
| 45 | 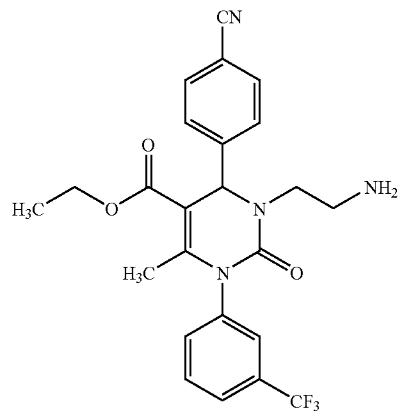 | Example 1; 2-bromo-ethanamine hydrobromide; 2.5 equiv. NaH | 28 | 2.9 (2) | 473 |
| 46 | 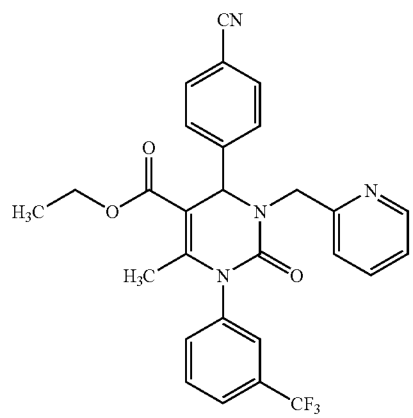 | Example 1; 2-(chloro-methyl)pyridine hydrochloride; 2.5 equiv. NaH | 37 | 4.0 (3) | 521 |
| 47 | 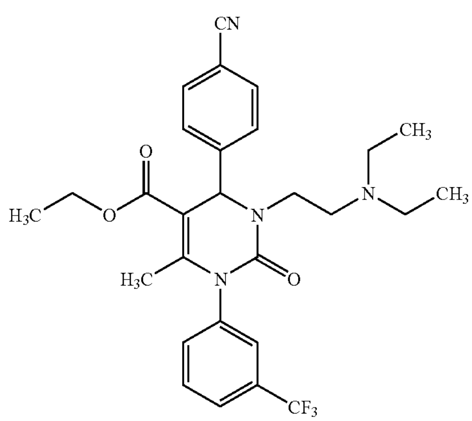 | Example 1; N-(2-bromo-ethyl)-N,N-diethylamine hydrobromide; 2.5 equiv. NaH | 82 | 2.98 (2) | 529 |

-continued

| Example No. | Structure | Starting materials | Yield [%] | R$_t$ [min] (method) | Mass [M + H]$^+$ |
|---|---|---|---|---|---|
| 48 | 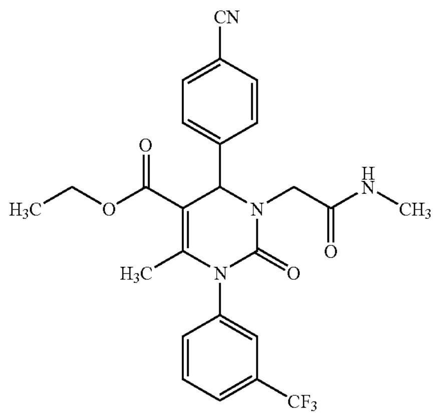 | Example 1; 2-bromo-N-methyl-acetamide; 2.5 equiv. NaH | 65 | 3.70 (2) | 501 |
| 49 | 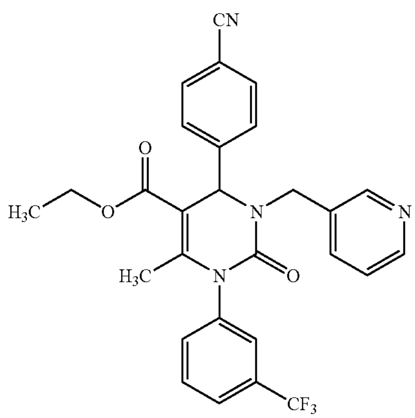 | Example 1; 3-(chloro-methyl)pyridine hydrochloride; 2.5 equiv. NaH | 15 | 3.68 (2) | 521 |
| 50 | 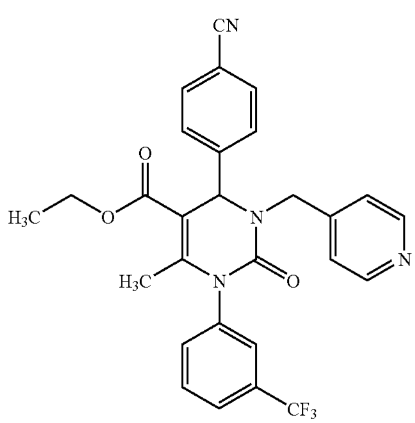 | Example 1; 4-(chloro-methyl)pyridine hydrochloride; 2.5 equiv. NaH | 21 | 3.47 (2) | 521 |

-continued

| Example No. | Structure | Starting materials | Yield [%] | R$_t$ [min] (method) | Mass [M + H]$^+$ |
|---|---|---|---|---|---|
| 51 | 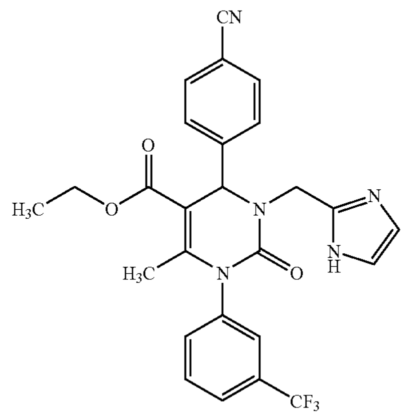 | Example 1; 2-(bromo-methyl)-1H-imidazole hydrobromide; 2.5 equiv. NaH | 6 | 2.97 (2) | 510 |
| 52 | 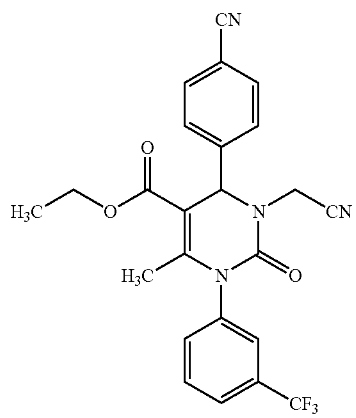 | Example 1; 3-chloro-methyl)-1,2,4-oxadiazole | 37 | 4.0 (3) | 469 |
| 53 | 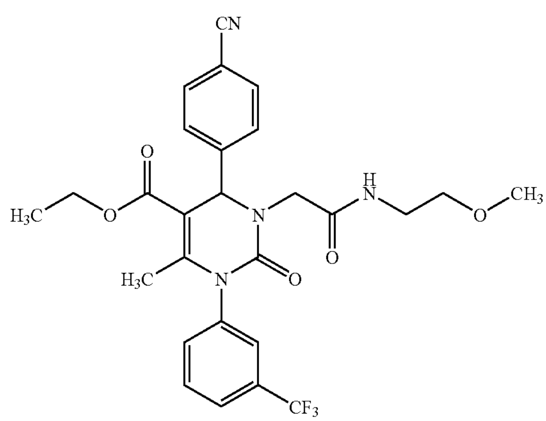 | Example 1; 2-bromo-N-(2-methoxyethyl)-acetamide | 91 | 3.77 (2) | 545 |

In analogy to the procedures for Examples 6-8, the following compounds are prepared:

| Example No. | Structure | Starting materials | Yield [%] | $R_t$ [min] (method) | Mass $[M + H]^+$ |
|---|---|---|---|---|---|
| 54 | (structure) | N-[3-(trifluoromethyl)phenyl]-urea; 4-cyano-benzaldehyde; methyl 3-oxobutanoate | 79 | 3.68 (2) | 416 |
| 55 | (structure) | N-[3-(trifluoromethyl)phenyl]-urea; 4-cyano-benzaldehyde; cyclopropylmethyl 3-oxobutanoate | 58 | 4.09 (2) | 456 |
| 56 | (structure) | N-[3-(trifluoromethyl)phenyl]-urea; 4-cyano-benzaldehyde; isopropyl 3-oxobutanoate | 85 | 4.03 (2) | 444 |

| Example No. | Structure | Starting materials | Yield [%] | $R_t$ [min] (method) | Mass $[M + H]^+$ |
|---|---|---|---|---|---|
| 57 | 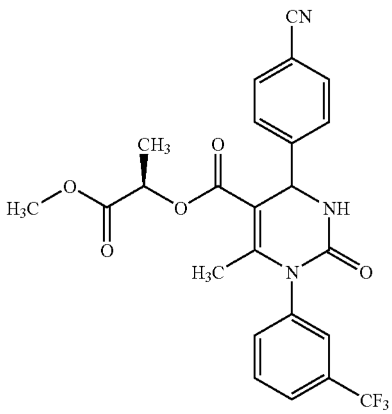 | N-[3-(trifluoro-methyl)phenyl]-urea; 4-cyano-benzaldehyde; (1R)-2-methoxy-1-methyl-2-oxo-ethyl 3-oxobutanoate | 73 | 3.82 (2) | 488 |
| 58 | 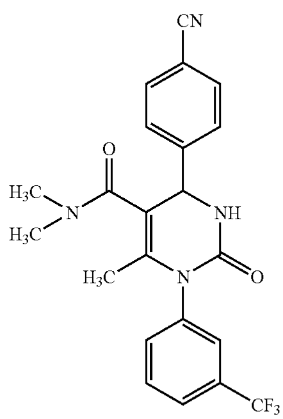 | N-[3-(trifluoro-methyl)phenyl]-urea; 4-cyano-benzaldehyde; N,N-dimethyl-3-oxobutanamide | 9 | 3.22 (2) | 429 |

Example 59

Ethyl 4-(4-cyanophenyl)-6-methyl-3-[2-(4-morpholinyl)-2-oxoethyl]-2-oxo-1-[3-(tri-fluoromethyl)phenyl]-1,2,3,4-tetrahydro-5-pyrimidinecarboxylate

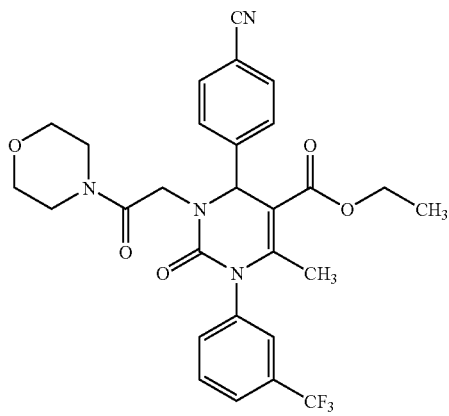

80 mg (0.16 mmol) of Example 44 are dissolved in 2 ml dimethylformamide, 16 mg (0.18 mmol) morpholine, 24 mg (0.18 mmol) 1-hydroxy-1H-benzotriazole hydrate and 20 mg (0.16 mmol) 4-dimethylaminopyridine are added. The reaction mixture is stirred at 0° C., then 35 mg (0.18 mmol) 1-(3-dimethylaminopropyl)-3-ethyl-carbodiimide hydrochloride are added. The reaction mixture is stirred at room temperature for 18 hours, then water and ethyl acetate are added. The organic phase is dried over sodium sulfate and evaporated to dryness in vacuo. If necessary, the product is further purified by column chromatography or preparative HPLC.

Yield: 78 mg (85%)

$^1$H-NMR (300 MHz, DMSO-$d_6$): δ=1.1 (t, 3H); 2.0 (s, 3H); 3.4 (m, 4H); 3.6 (m, 4H); 3.7 (d, 1H); 4.1 (m, 2H); 4.5 (d, 1H); 5.5 (s, 1H); 7.6 (m, 5H); 7.8 (m, 1H); 7.9 (m, 2H) ppm.

In analogy to the procedure for Example 59, the following compounds are prepared:

| Example No. | Structure | Starting materials | Yield [%] | $R_t$ [min] (method) | Mass $[M + H]^+$ |
|---|---|---|---|---|---|
| 60 | 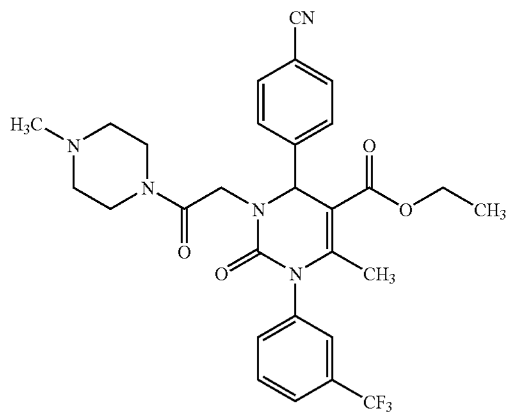 | Example 44; N-methyl-piperazine | 90 | 2.93 (2) | 570 |
| 61 | 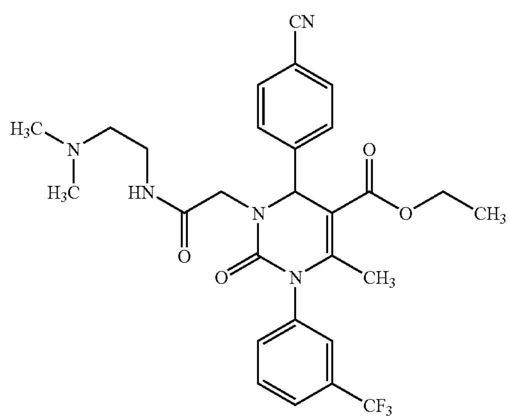 | Example 44; N-(2-amino-ethyl)-N,N-dimethylamine | 87 | 2.93 (2) | 558 |
| 62 | 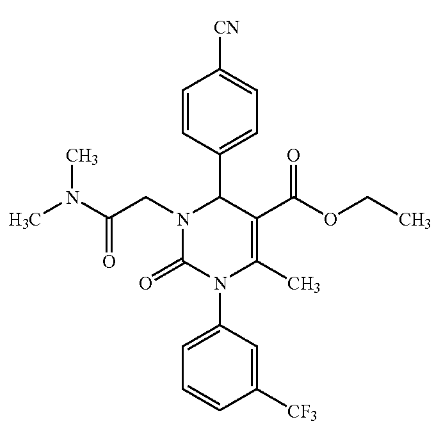 | Example 44; dimethylamine (2 M in THF) | 83 | 3.84 (2) | 515 |

In analogy to the procedures for Examples 6-8, the following compounds are prepared:

| Example No. | Structure | Starting materials | Yield [%] | $R_t$ [min] (method) | Mass $[M + H]^+$ |
|---|---|---|---|---|---|
| 63 | 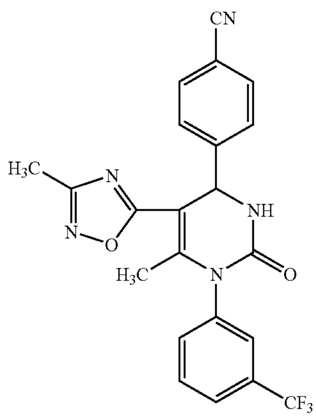 | N-[3-trifluoromethyl)phenyl]-urea; 4-cyanobenzaldehyde; 1-(3-methyl-1,2,4-oxadiazol-5-yl)acetone | 23 | 3.80 (3) | 440 |
| 64 | 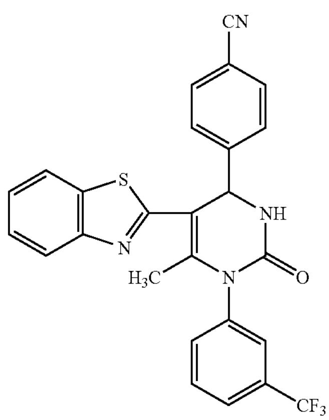 | N-[3-trifluoromethyl)phenyl]-urea; 4-cyanobenzaldehyde; 1-(1,3-benzothiazol-2-yl)-acetone | 23 | 4.42 (2) | 491 |
| 65 | 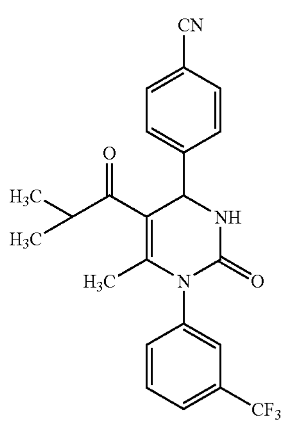 | N-[3-trifluoromethyl)phenyl]-urea; 4-cyanobenzaldehyde; 5-methyl-2,4-hexanedione | 33 | 4.3 (1) | 428 |

-continued

| Example No. | Structure | Starting materials | Yield [%] | R$_t$ [min] (method) | Mass [M + H]$^+$ |
|---|---|---|---|---|---|
| 66 | 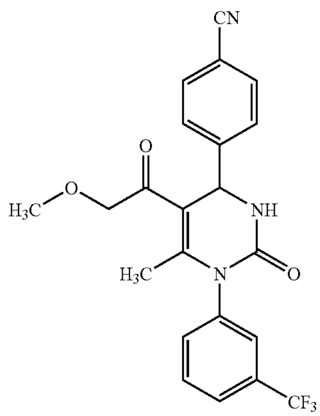 | N-[3-trifluoro-methyl)phenyl]-urea; 4-cyano-benzaldehyde; 1-methoxy-2,4-pentanedione | 3 | 3.47 (2) | 430 |
| 67 | 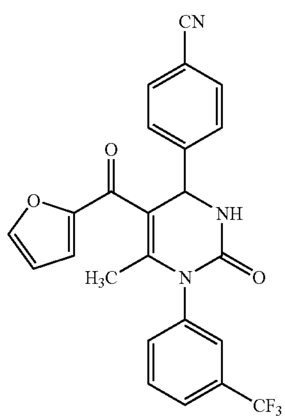 | N-[3-trifluoro-methyl)phenyl]-urea; 4-cyano-benzaldehyde; 1-(2-furyl)-1,3-butanedione | 13 | 3.70 (2) | 452 |
| 68 | 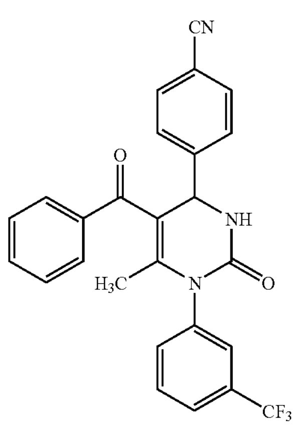 | N-[3-trifluoro-methyl)phenyl]-urea; 4-cyano-benzaldehyde; 1-phenyl-1,3-butanedione | 14 | 4.03 (2) | 462 |

| Example No. | Structure | Starting materials | Yield [%] | $R_t$ [min] (method) | Mass $[M + H]^+$ |
|---|---|---|---|---|---|
| 69 | 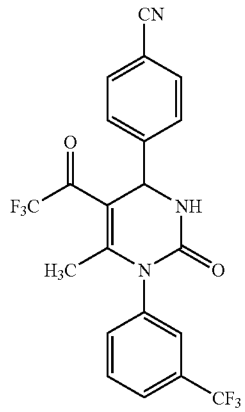 | N-[3-trifluoromethyl)phenyl]-urea; 4-cyanobenzaldehyde; 1,1,1-trifluoro-2,4-pentanedione | 5 | 3.9 (3) | 454 |

$^1$H-NMR (200 MHz, DMSO-$d_6$): δ=1.8 (s, 3H); 5.4 (d, 1H); 7.2 (br. s, 1H); 7.4 (br. s, 1H); 7.6 (m, 5H); 7.7 (m, 1H); 7.9 (m, 2H); 8.1 (d, 1H) ppm.

Example 70

4-(4-Cyanophenyl)-6-methyl-2-oxo-1-[3-(trifluoromethyl)phenyl]-1,2,3,4-tetrahydro-5-pyrimidinecarboxamide

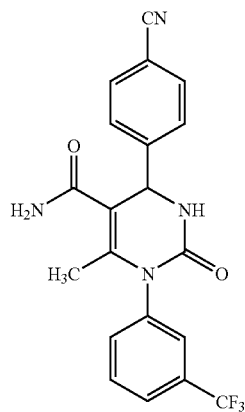

200 mg (0.5 mmol) of Example 11 are dissolved in 5 ml tetrahydrofuran and 6 mg (0.05 mmol) 4-N,N-dimethylaminopyridine, 77 mg (0.6 mmol) N,N-diisopropyl-ethylamine and 115 mg (0.6 mmol) benzotriazol-1-yloxy-trispyrrolidino)phosphonium hexafluorophosphate are added. The reaction mixture is stirred at room temperature for 15 minutes, then 5 ml (2.5 mmol) ammonia (as 0.5 M solution in dioxane) are added. The reaction mixture is stirred at room temperature for 1 hour, then water and ethyl acetate are added. The organic phase is dried over sodium sulfate and evaporated to dryness in vacuo. The product is further purified by preparative HPLC.

Yield: 55 mg (28% of th.)

Example 71

(+)-4-(4-Cyanophenyl)-6-methyl-2-oxo-1-[3-(trifluoromethyl)phenyl]-1,2,3,4-tetrahydro-5-pyrimidinecarboxylic acid

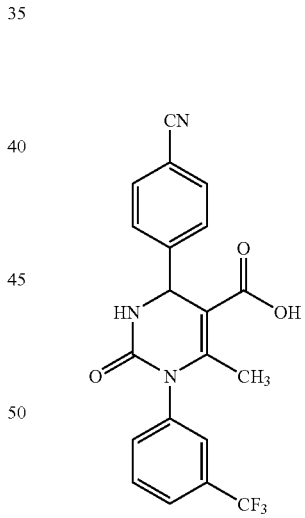

The enantiomers of Example 11 are separated by preparative HPLC on a chiral phase [column KBD 8361 (chiral silica gel selector based on monomer N-methacryloyl-L-leucine-1-menthylamide, cf. EP-A-379 917), 250 mm×20 mm, eluent: ethyl acetate→methanol→ethyl acetate, flow 25 ml/min, temperature 23° C., detection 254 nm].

$^1$H-NMR (300 MHz, DMSO-$d_6$): δ=2.0 (s, 3H); 5.4 (d, 1H); 7.6 (m, 1H); 7.6 (m, 2H); 7.7 (m, 1H); 7.8 (m, 1H); 7.9 (m, 3H); 8.3 (d, 1H); 12.5 (s, 1H) ppm.

$[α]^{20}$=+2.5° (λ=589 nm, methanol, c=505 mg/100 ml)

Example 72

(+)-2-Hydroxyethyl 4-(4-cyanophenyl)-6-methyl-2-oxo-1-[3-(trifluoromethyl)-phenyl]-1,2,3,4-tetrahydro-5-pyrimidinecarboxylate

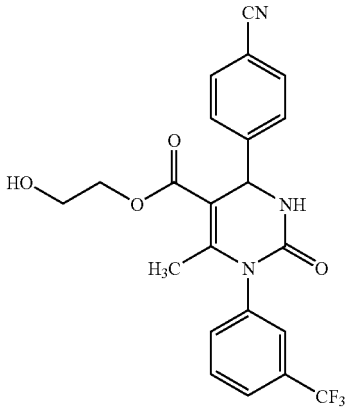

Under argon, 1560 mg (3.89 mmol) of the compound of Example 71 are added to 19.6 ml DMF. After addition of 1.095 ml (7.86 mmol) triethylamine and 1.11 ml (15.7 mmol) 2-bromoethanol, the reaction mixture is stirred at ca. 70° C. for 8 hours. After cooling, the reaction mixture is concentrated in vacuo. The residue is taken up in ethyl acetate and washed with water. After drying with magnesium sulfate, the organic phase is evaporated in vacuo. The residue is taken up in 8 ml methanol and purified by preparative HPLC (column: Nucleosil 100-5 C 18 Nautilus, 20×50 mm, 5 μm; solvent A: acetonitrile, solvent B: water+0.3% formic acid; gradient: 0 min 10% A, 2 min 10% A, 6 min 90% A, 7 min 90% A, 7.1 min 10% A, 8 min 10% A; wavelength: 220 mm; injection volume: ca. 500 μl; number of injections: 18). The product containing fractions are combined and lyophilized.

Yield: 1290 mg (74.5% of th.)
MS (EI): m/z=446 (M+H)$^+$
$^1$H-NMR (300 MHz, DMSO-d$_6$): δ=2.05 (d, 3H); 3.5 (quartett, 211); 3.95-4.15 (m, 2H); 4.75 (tr, 1H); 5.45 (d, 1H); 7.55-7.75 (m, 5H); 7.75 (d, 1H); 7.85 (d, 2H); 8.35 (d, 1H) ppm.
$[α]^{21}$=+14.30 (=589 nm, methanol, c=455 mg/100 ml).

Example 73

5-{5-Acetyl-6-methyl-2-oxo-1-[3-(trifluoromethyl)phenyl]-1,2,3,4-tetrahydro-4-pyrimidinyl}-2-pyridinecarbonitrile

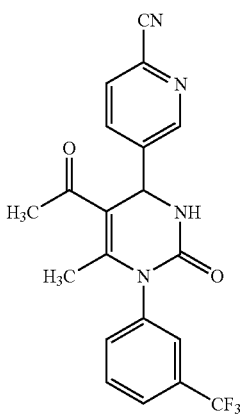

To a stirred solution of Example 3A (75 mg, 0.57 mmol) in tetrahydrofuran (5 ml) is given 2,4-pentandione (57 mg, 0.57 mmol), N-[3-(trifluoromethyl)phenyl]urea (116 mg, 0.57 mmol) and polyphosphoric acid ethyl ester (200 mg) [freshly prepared according to the procedure of Cava et al., J. Org. Chem. 34, 2665 (1969)]. The reaction mixture is refluxed for 24 hours after which time the solution is diluted with DMSO (2 ml) and purified by preparative HPLC.

Yield: 101 mg (44% of th.)
$^1$H-NMR (200 MHz, DMSO-d$_6$): δ=2.02 (s, 3H); 2.24 (s, 3H); 5.54 (d, 1H); 7.52-7.90 (m, 4H); 8.08 (d, 2H); 8.50 (d, 1H); 8.81 (s, 1H) ppm.

Example 74

(+)-5-{5-Acetyl-6-methyl-2-oxo-1-[3-(trifluoromethyl)phenyl]-1,2,3,4-tetrahydro-4-pyrimidinyl}-2-pyridinecarbonitrile

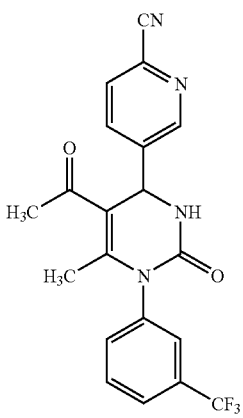

The enantiomers of Example 73 are separated by preparative HPLC on a chiral phase [column KBD 8361 (chiral silica gel selector based on monomer N-methacryloyl-L-leucine-1-menthylamide, cf. EP-A-379 917), 250 mm×20 mm, eluent: ethyl acetate→methanol→ethyl acetate, flow 25 ml/min, temperature 23° C., detection 254 nm].

$^1$H-NMR (300 MHz, CDCl$_3$): δ=2.06 (s, 3H); 2.35 (s, 3H); 5.69 (d, 1H); 6.02 (d, 1H); 7.29-7.50 (m, 2H); 7.57-7.75 (m, 3H); 7.83 (dd, 1H); 8.74 (d, 1H) ppm.

MS (ESIpos): m/z 401 (M+H)$^+$
$[α]^{20}$=+25.1° (δ=589 nm, methanol, c=505 mg/100 ml).

Example 75

2-(2-Pyridinyl)methyl 4-(4-cyanophenyl)-6-methyl-2-oxo-1-[3-(trifluoromethyl)-phenyl]-1,2,3,4-tetrahydro-5-pyrimidinecarboxylate

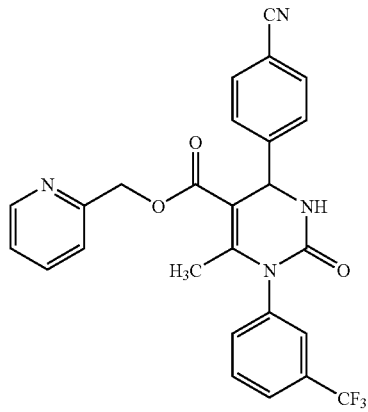

To a solution of 40.1 mg (0.1 mmol) of the compound of Example 11 in 0.4 ml dry dimethylformamide are added 48.6 mg (0.3 mmol) N,N-carbonyldiimidazole. After allowing the reaction mixture to stand for one hour, the reaction mixture is diluted with water and extracted with dichloromethane. After drying with magnesium sulfate, the solvent is evaporated off in vacuo. To the residue are added to 0.5 ml (2-pyridinyl)methanol. The reaction mixture is stirred at approx. 100° C. for 1 hour. After cooling, the reaction mixture is purified by preparative HPLC (column: Nucleosil 100-5 C 18 Nautilus 20 mm×50 mm, 5 μm; solvent A: acetonitrile, solvent B: water+0.1% formic acid; gradient: 0 min 10% A, 2 min 10% A, 6 min 90% A, 7 min 90% A, 7.1 min 10% A, 8 min 10% A; flow rate 25 ml/min; wavelength: 220 nm; injection volume: approx. 550 μl; number of injections: 1). The product containing fractions are combined and concentrated in vacuo.

Yield: 17 mg (34.5% of th.)

MS (EI): m/z=493 (M+H)$^+$ $^1$H-NMR (300 MHz, DMSO-d$_6$): δ=2.1 (d, 3H); 5.15 (dd, 2H); 5.45 (d, 1H); 7.05 (d, 1H); 7.3 (dd, 1H); 7.5-7.85 (m, 9H); 8.35 (d, 1H); 8.5 (d, 2H) ppm.

Example 76

2-(3-Pyridinyl)ethyl 4-(4-cyanophenyl)-6-methyl-2-oxo-1-[3-(trifluoromethyl)-phenyl]-1,2,3,4-tetrahydro-5-pyrimidinecarboxylate

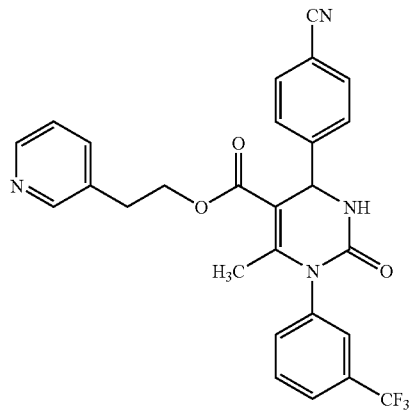

To a solution of 60.2 mg (0.15 mmol) of the compound of Example 11 in 0.57 ml dry dimethylformamide are added 72.9 mg (0.45 mmol) N,N-carbonyldiimidazole. After allowing the reaction mixture to stand for one hour, the reaction mixture is diluted with water and extracted with ethylacetate. After drying with magnesium sulfate, the solvent is evaporated off in vacuo. To the residue are added 185 mg (1.5 mmol) 2-(3-pyridyl)ethanol and 20 μl (0.27 mol) triethylamine. The reaction mixture is stirred for one hour at 100° C. Then the reaction mixture is diluted with 0.4 ml methanol, filtered and purified by preparative HPLC (column: Nucleosil 100-5 C 18 Nautilus 20 mm×50 mm, 5 μm; solvent A: acetonitrile, solvent B: water+0.1% formic acid; gradient: 0 min 10% A, 2 min 10% A, 6 min 90% A, 7 min 90% A, 7.1 min 10% A, 8 min 10% A; flow rate 25 ml/min; wavelength: 220 nm; injection volume: approx. 550 μl; number of injections: 1). The product containing fractions are combined and concentrated in vacuo.

Yield: 44 mg (57.9% of th.)

LC-MS (EI, method 5): m/z=507 (M+H)$^+$, R$_t$=3.19 min.

Example 77

4-(4-Cyanophenyl)-3,6-dimethyl-2-oxo-1-[3-(trifluoromethyl)phenyl]-1,2,3,4-tetrahydro-5-pyrimidinecarboxylic acid

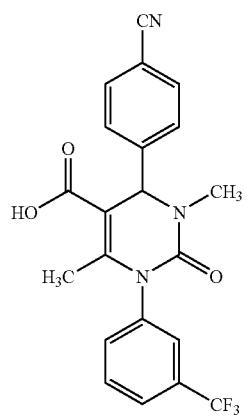

4.1 g (9.25 mmol) of Example 14 are dissolved in 100 ml ethanol. To this solution 6.2 ml (27.6 mmol) of a solution of potassium hydroxide in water (25% by weight) are added. The reaction mixture is allowed to stand at room temperature for 18 hours. Then further 12.4 ml (55.2 mmol) of a solution of potassium hydroxide in water (25% by weight) are added and the reaction mixture is stirred for 2 hours. The reaction mixture is diluted with water and extracted three times with ethyl acetate. The aqueous phase is acidified with 1 N hydrochloric acid and extracted with ethyl acetate. This last extract is dried over magnesium sulfate and evaporated off in vacuo. The residue is purified by column chromatography on silica with cyclohexane/ethyl acetate as eluent.

Yield: 1.5 g (39% of th.)

MS (EI): m/z=416 (M+H)$^+$ $^1$H-NMR (300 MHz, DMSO-d$_6$): δ=2.0 (s, 3H); 2.8 (s, 3H); 5.5 (d, 1H); 7.6-7.8 (m, 6H); 7.9 (d, 2H); 12.6 (s, 1H) ppm.

In analogy to the procedure for Example 76, the following compounds are prepared:

| Example No. | Structure | Starting materials | Yield [%] | R$_t$ [min] (method) | Mass [M + H]$^+$ |
|---|---|---|---|---|---|
| 78 | 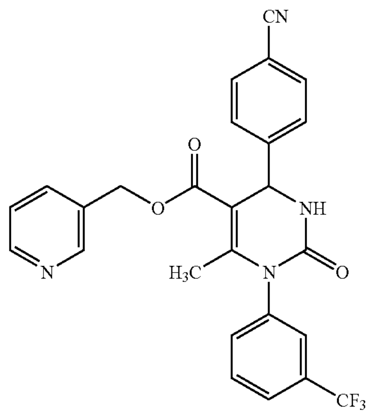 | Example 11; 3-pyridinyl-methanol | 56.9 | 3.45 (5) | 493 |
| 79 | 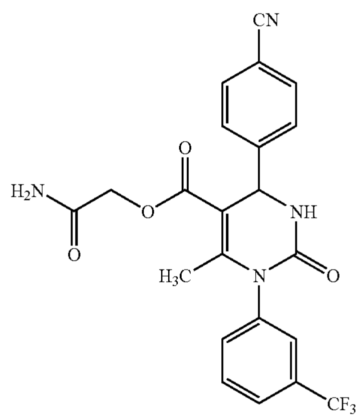 | Example 11; 2-hydroxy-acetamide[1)] | 61.1 | 3.38 (5) | 459 |
| 80 | 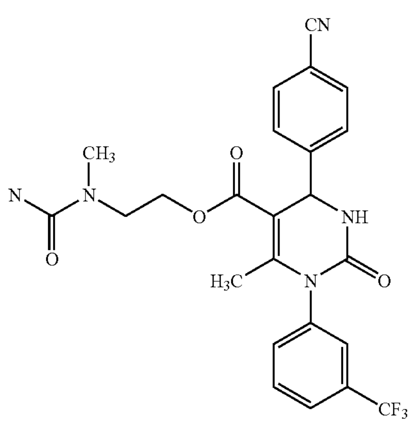 | Example 11; 2-hydroxyethyl-(methyl)form-amide | 80.9 | 3.5 (5) | 487 |

-continued

| Example No. | Structure | Starting materials | Yield [%] | $R_t$ [min] (method) | Mass $[M + H]^+$ |
|---|---|---|---|---|---|
| 81 | 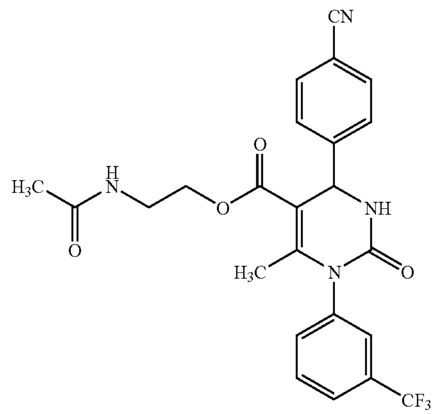 | Example 11; 2-hydroxyethyl-acetamide | 56.2 | 3.44 (5) | 487 |
| 82 | 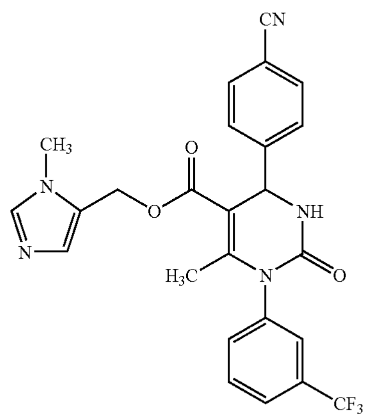 | Example 11; (1-methyl-1H-imidazol-5-yl)-methanol[1] | 45.8 | 2.87 (5) | 496 |
| 83 | 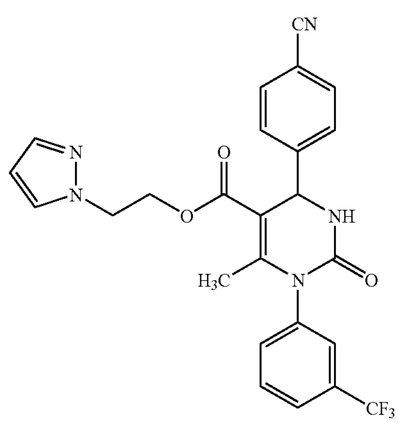 | Example 11; 2-(1H-pyrazol-1-yl)ethanol | 60.6 | 3.7 (5) | 496 |

-continued

| Example No. | Structure | Starting materials | Yield [%] | $R_t$ [min] (method) | Mass $[M + H]^+$ |
|---|---|---|---|---|---|
| 84 | 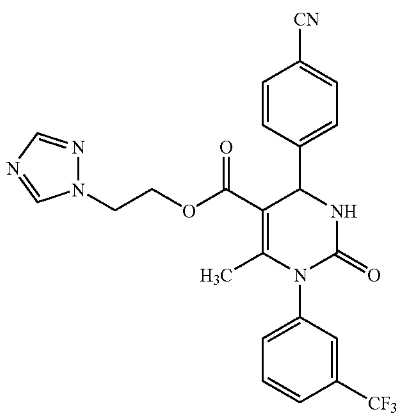 | Example 11; 2-(1H-1,2,4-triazol-1-yl)-ethanol[1)] | 67.1 | 3.48 (5) | 497 |
| 85 | 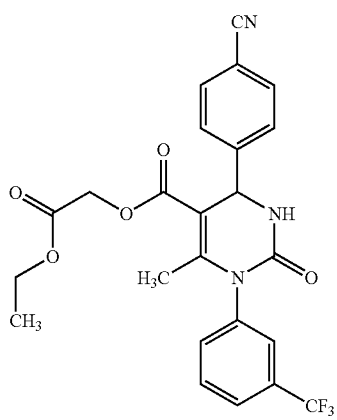 | Example 11; 2-hydroxyethyl acetate | 56.1 | 3.98 (5) | 488 |
| 86 | 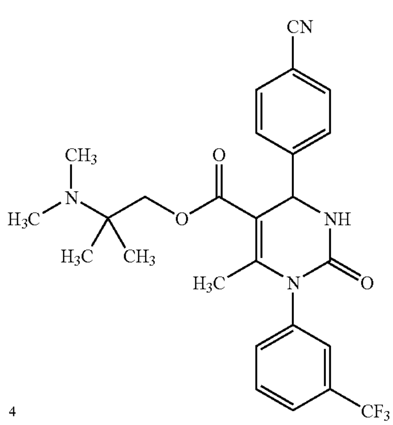 | Example 11; 2-(dimethyl-amino)-2-methyl-1-propanol | 34.6 | 2.9 (5) | 502 |

-continued

| Example No. | Structure | Starting materials | Yield [%] | $R_t$ [min] (method) | Mass [M + H]$^+$ |
|---|---|---|---|---|---|
| 87 | 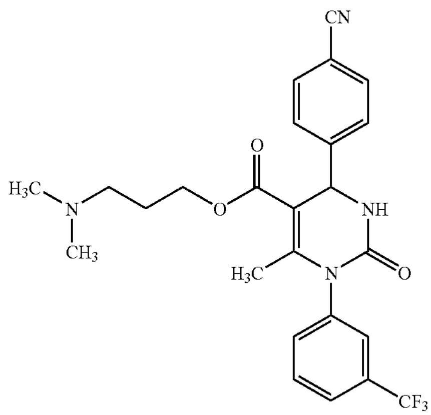 | Example 11; 3-(dimethylamino)propanol | 54.8 | 2.86 (5) | 487 |
| 88 | 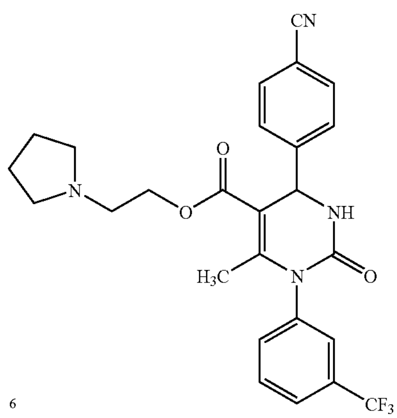 | Example 11; 2-(1-pyrrolidinyl)-ethanol | 56.2 | 2.86 (5) | 500 |
| 89 | 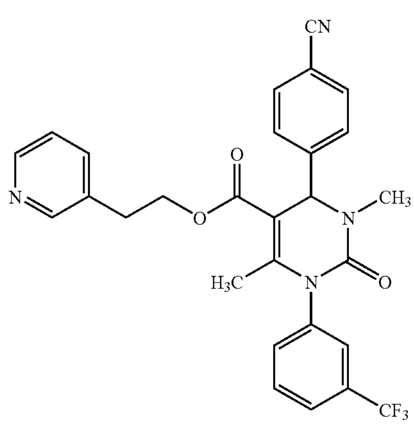 | Example 77; 2-(3-pyridinyl)-ethanol | 58.9 | 3.36 (5) | 522 |

-continued

| Example No. | Structure | Starting materials | Yield [%] | $R_t$ [min] (method) | Mass [M + H]$^+$ |
|---|---|---|---|---|---|
| 90 | 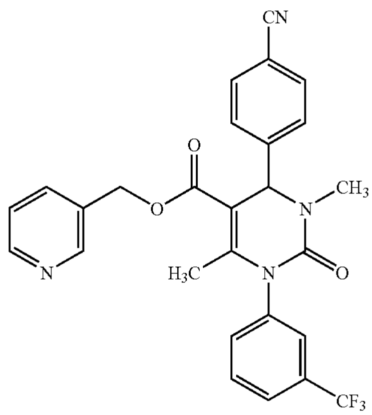 | Example 77; (3-pyridinyl)-methanol | 61.9 | 3.64 (5) | 507 |
| 91 | 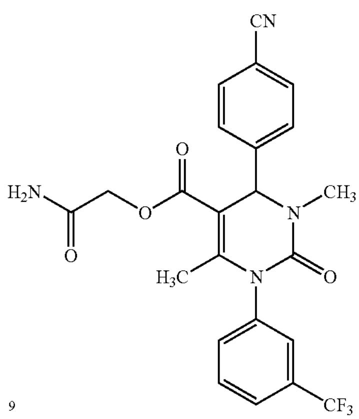 | Example 77; 2-hydroxy-acetamide[1] | 53.6 | 3.54 (5) | 473 |
| 92 | 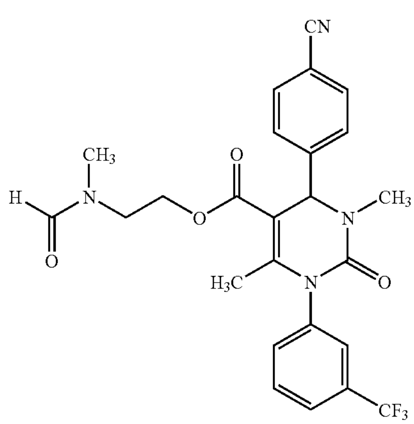 | Example 77; 2-hydroxyethyl-(methyl)form-amide | 54.6 | 3.68 (5) | 501 |

-continued

| Example No. | Structure | Starting materials | Yield [%] | R$_t$ [min] (method) | Mass [M + H]$^+$ |
|---|---|---|---|---|---|
| 93 | (structure) | Example 77; 2-hydroxyethyl-acetamide | 66.6 | 3.59 (5) | 501 |

| Example No. | Structure | Starting materials | Yield [%] | R$_t$ [min] (method) | Mass [M + H]$^+$ |
|---|---|---|---|---|---|
| 94 | (structure) | Example 77; (1-methyl-1H-imidazol-5-yl)-methanol[1] | 34.0 | 3.02 (5) | 510 |
| 95 | (structure) | Example 77; 2-(1H-pyrazol-1-yl)ethanol | 61.5 | 3.91 (5) | 510 |

-continued

| Example No. | Structure | Starting materials | Yield [%] | $R_t$ [min] (method) | Mass $[M+H]^+$ |
|---|---|---|---|---|---|
| 96 | E24 | Example 77; 2-(1H-1,2,4-triazol-1-yl)-ethanol[1)] | 71.8 | 3.64 (5) | 511 |
| 97 | 5 | Example 77; 2-hydroxyethyl acetate | 53.2 | 4.12 (5) | 502 |
| 98 | 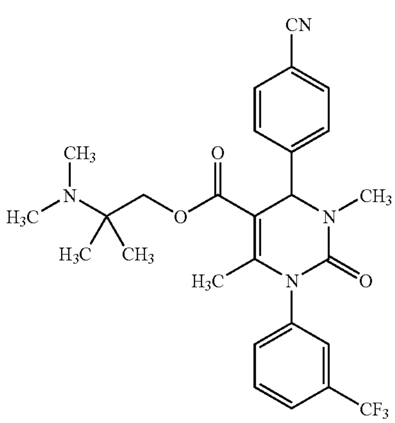 | Example 77; 2-(dimethyl-amino)-2-methyl-1-propanol | 25.9 | 3.02 (5) | 516 |

-continued

| Example No. | Structure | Starting materials | Yield [%] | $R_t$ [min] (method) | Mass $[M + H]^+$ |
|---|---|---|---|---|---|
| 99 | 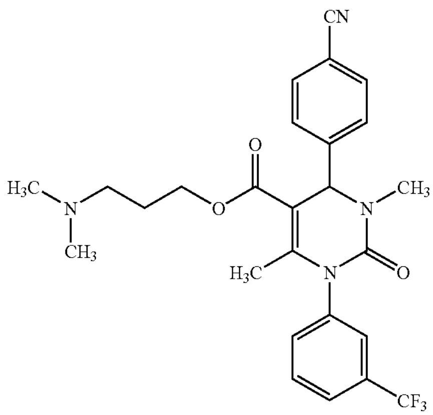 | Example 77; 3-(dimethyl-amino)propanol | 54.6 | 2.98 (5) | 502 |
| 100 | 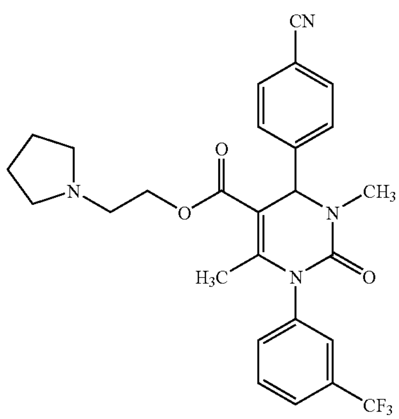 | Example 77; 2-(1-pyrrolidinyl)-ethanol | 55.9 | 2.98 (5) | 514 |
| 101 | 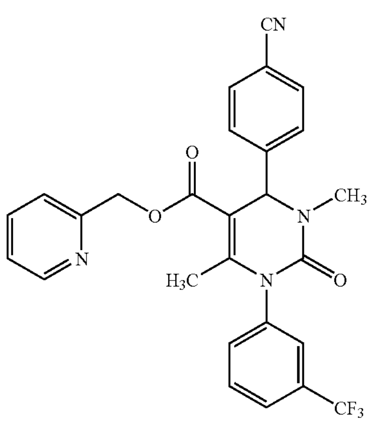 | Example 77; (2-pyridinyl)-methanol | 67.1 | 3.91 (5) | 507 |

[1] in this case the alcohol used is a solid and the reaction is conducted in the presence of 0.4 ml DMF

Example 102

Ethyl 4-(4-cyanophenyl)-1-(3,5-dichlorophenyl)-6-methyl-2-oxo-1,2,3,4-tetrahydro-5-pyrimidinecarboxylate

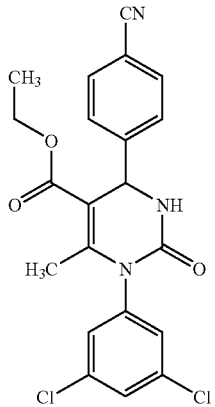

Under argon, 30.8 mg (0.15 mmol) N-(3,5-dichlorophenyl)urea are stirred together with 39.3 mg (0.3 mmol) 4-formylbenzonitrile, 39 mg (0.3 mmol) ethyl 3-oxo-butanoate and 90 mg trimethylsilylpolyphosphate in 0.5 ml dioxan at 80° C. for 4 hours. After adding a small amount of DMSO, the reaction mixture is filtered and purified by preparative HPLC (column: Agilent Zorbax Extend C18 20 mm×50 mm, 5 µm; solvent A: acetonitrile, solvent B: water+0.1% conc. aq. ammonia; gradient: 0 min 10% A, 2 min 10% A, 6 min 90% A, 7 min 90% A, 7.1 min 10% A, 8 min 10% A; flow rate 25 ml/min; wavelength: 220 nm; injection volume: approx. 500 µl; number of injections: 1). The product containing fractions are combined and concentrated in vacuo.

Yield: 38.1 mg (59% of th.)

LC-MS (EI, method 7): m/z=431 (M+H)$^+$, $R_t$=4.14 min.

Example 103

Ethyl 6-methyl-4-(3-nitrophenyl)-2-oxo-1-[3-(trifluoromethyl)phenyl]-1,2,3,4-tetra-hydro-5-pyrimidinecarboxylate

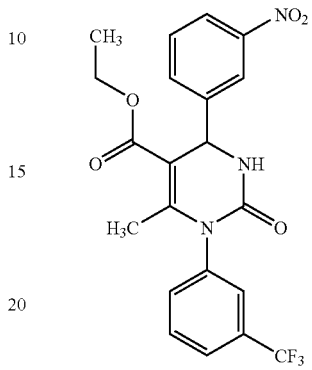

30.6 mg (0.15 mmol) N-[3-(trifluoromethyl)phenyl]urea are shaken together with 45.3 mg (0.3 mmol) 3-nitrobenzaldehyde, 39 mg (0.3 mmol) ethyl 3-oxobutanoate and 90 mg polyphosphoric acid ethyl ester [freshly prepared according to the procedure of Cava et al., J. Org. Chem. 34, 2665 (1969)] in 0.5 ml dioxan and 0.1 ml DMF at 80° C. for 18 hours. After adding 200 µl DMF, the reaction mixture is filtered and purified by preparative HPLC (column: Nucleosil 100-5 C 18 Nautilus 20 mm×50 mm, 5 µm; solvent A: acetonitrile, solvent B: water+0.1% formic acid; gradient: 0 min 10% A, 2 min 10% A, 6 min 90% A, 7 min 90% A, 7.1 min 10% A, 8 min 10% A; flow rate 25 ml/min; wavelength: 220 nm; injection volume: approx. 800 µl; number of injections: 1). The product containing fractions are combined and concentrated in vacuo.

Yield: 34 mg (50.4% of th.)

LC-MS (EI, method 6): m/z=450 (M+H)$^+$, $R_t$=3.94 min.

In analogy to the procedure for Example 102, the following compounds are prepared:

| Example No. | Structure | Starting materials | Yield [%] | $R_t$ [min] (method) | Mass [M + H]$^+$ |
|---|---|---|---|---|---|
| 104 | 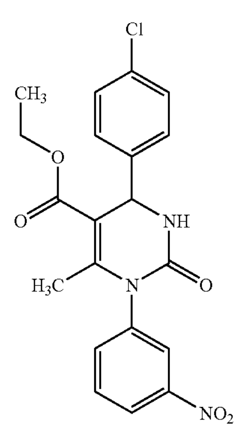 | N-(3-nitrophenyl)urea; 4-chlorobenzaldehyde; ethyl 3-oxobutanoate | 70.5 | 3.65 (6) | 417 |

-continued

| Example No. | Structure | Starting materials | Yield [%] | $R_t$ [min] (method) | Mass [M + H]⁺ |
|---|---|---|---|---|---|
| 105 | 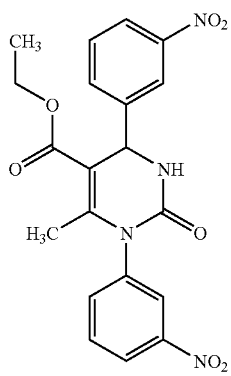 | N-(3-nitro-phenyl)urea; 3-nitrobenz-aldehyde; ethyl 3-oxobutanoate | 81.3 | 3.61 (6) | 427 |
| 106 | 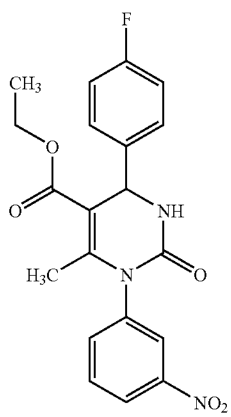 | N-(3-nitro-phenyl)urea; 4-fluorobenz-aldehyde; ethyl 3-oxobutanoate | 56.8 | 3.63 (6) | 400 |
| 107 | 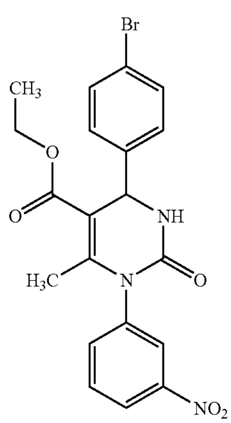 | N-(3-nitro-phenyl)urea; 4-bromobenz-aldehyde; ethyl 3-oxobutanoate | 69.5 | 4.02 (5) | 461 |

Example 108

4-(4Cyanophenyl)-6-methyl-2-oxo-1-[3-(trifluoromethyl)phenyl]-1,2,3,4-tetrahydro-pyrimidine-5-carboxylic acid 2-cyanoethyl ester

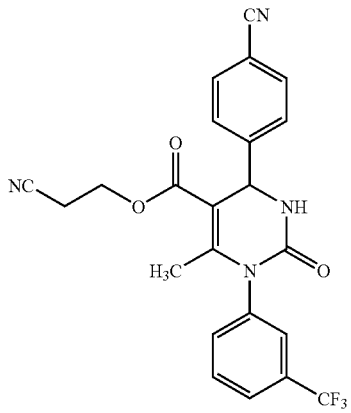

9.87 g (48.3 mmol) N-[3-(trifluoromethyl)phenyl]urea, 12.68 g (96.68 mmol) 4-cyanobenzaldehyde, 15 g (96.68 mmol) (2-cyanoethyl) 3-oxobutanoate and 37.5 g polyphosphoric acid ethyl ester are suspended in 250 ml of THF. The mixture is stirred at reflux for 18 hours. After cooling down to room temperature, the solvent is removed in vacuo and the residue is purified by column chromatography on silica with cyclohexane/ethyl acetate as eluent.

Yield: 25 g (100% of th.)

$^1$H-NMR (200 Mz, DMSO-d$_6$): δ=2.1 (s, 3H); 2.8 (m, 2H); 4.2 (m, 2H); 5.4 (d, 1H); 7.6 (m, 4H); 7.7 (m, 2H); 7.9 (m, 2H); 8.5 (d, 1H) ppm.

Example 109

4-(4-Cyanophenyl)-6-methyl-2-oxo-1-[3-(trifluoromethyl)phenyl]-1,2,3,4-tetrahydro-pyrimidine-5-carbonitrile

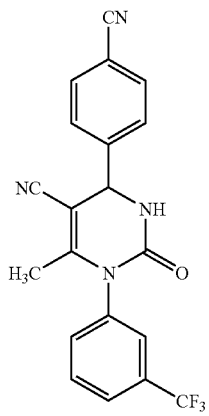

0.609 g (1.52 mmol) of Example 70 are dissolved in 60 ml THF and 1.24 g (12.93 mmol) (methoxycarbonylsulfamoyl)-triethylammonium-N-betaine are added. The reaction mixture is stirred at room temperature for 1 hour, the solvent is removed in vacuo and the residue is purified by column chromatography on silica with dichloromethane/methanol mixtures as eluent.

Yield: 249 mg (43% of th.)

$^1$H-NMR (300 Mz, DMSO-d$_6$): δ=1.8 (s, 3H); 5.4 (d, 1H); 7.7 (m, 4H); 7.8 (m, 2H); 8.0 (m, 2H), 8.4 (d, 1H) ppm.

Example 110

Ethyl 6-methyl-4-(4-nitrophenyl)-2-oxo-1-[3-(trifluoromethyl)phenyl]-1,2,3,4-tetra-hydropyrimidine-5-carboxylate

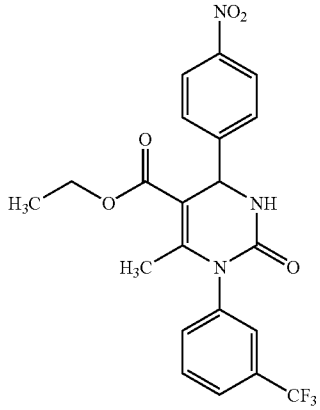

7.84 g (38.4 mmol) N-[3-(trifluoromethyl)phenyl]urea, 5.81 g (38.4 mmol) 4-nitro-benzaldehyde, 5.0 g (38.4 mmol) ethyl 3-oxobutanoate and 15 g polyphosphoric acid ethyl ester are suspended in 100 ml of THF. The mixture is stirred at reflux for 18 hours. After cooling down to room temperature, the solvent is removed in vacuo and the residue is purified by column chromatography on silica with toluene/etiyl acetate as eluent.

Yield: 8.75 g (51% of th.)

$^1$H-NMR (200 MHz, DMSO-d$_6$): δ=1.1 (t, 3H), 2.1 (s, 3H); 4.0 (m, 2H); 5.4 (d, 1H); 7.5-7.8 (m, 6H); 8.3 (m, 2H); 8.5 (d, 1H) ppm.

Example 111

5-Acetyl-6-methyl-4-(4-nitrophenyl)-2-oxo-1-[3-(trifluoromethyl)phenyl]-1,2,3,4-tetrahydropyrimidine

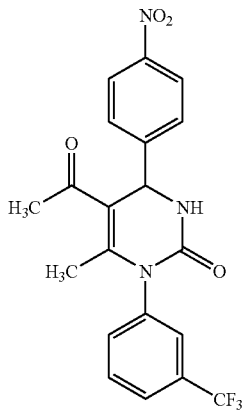

0.407 g (2.0 mmol) N-[3-(trifluoromethyl)phenyl]urea, 0.302 g (2.0 mmol) 4-nitro-benzaldehyde, 0.2 g (2.0 mmol) 2,4-pentanedione and 0.4 g polyphosphoric acid ethyl ester are suspended in 20 ml of THF. The mixture is stirred at reflux for 18 hours. After cooling down to room temperature, the solvent is removed in vacuo and the residue is purified by column chromatography on silica with cyclohexane/ethyl acetate as eluent.

Yield: 0.302 g (36% of th.)

$^1$H-NMR (200 MHz, DMSO-$d_6$): δ2.0 (s, 3H); 2.2 (s, 3H); 5.5 (d, 1H); 7.5-7.8 (m, 6H); 8.3 (m, 2H); 8.5 (d, 1H) ppm.

C. OPERATIVE EXAMPLES RELATING TO PHARMACEUTICAL COMPOSITIONS

The compounds according to the invention can be converted into pharmaceutical preparations as follows:

Tablet

Composition 100 mg of the compound of Example 1, 50 mg of lactose (monohydrate), 50 mg of maize starch (native), 10 mg of polyvinylpyrrolidone (PVP 25) (from BASF, Ludwigshafen, Germany) and 2 mg of magnesium stearate.

Tablet weight 212 mg, diameter 8 mm, curvature radius 12 mm.

Preparation

The mixture of active component, lactose and starch is granulated with a 5% solution (m/m) of the PVP in water. After drying, the granules are mixed with magnesium stearate for 5 min. This mixture is moulded using a customary tablet press (tablet format, see above). The moulding force applied is typically 15 kN.

Orally Administrable Suspension

Composition 1000 mg of the compound of Example 1, 1000 mg of ethanol (96%), 400 mg of Rhodigel (xanthan gum from FMC, Pennsylvania, USA) and 99 g of water.

A single dose of 100 mg of the compound according to the invention is provided by 10 ml of oral suspension.

Preparation

The Rhodigel is suspended in ethanol and the active component is added to the suspension. The water is added with stirring. Stirring is continued for about 6 h until the swelling of the Rhodigel is complete.

We claim:

1. A compound of the general formula (I)

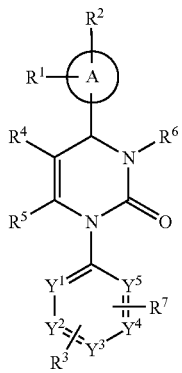

wherein
A represents an aryl or heteroaryl ring,
$R^1$, $R^2$ and $R^3$ independently from each other represent hydrogen, halogen, nitro, cyano, $C_1$-$C_6$-alkyl, hydroxy or $C_1$-$C_6$-alkoxy, wherein $C_1$-$C_6$-alkyl and $C_1$-$C_6$-alkoxy can be further substituted with one to three identical or different radicals selected from the group consisting of halogen, hydroxy and $C_1$-$C_4$-alkoxy, $R^4$ represents trifluoromethylcarbonyl, $C_1$-$C_6$-alkylcarbonyl, $C_1$-$C_6$-alkoxycarbonyl, $C_1$-$C_6$-alkenoxycarbonyl, hydroxycarbonyl, aminocarbonyl, mono- or di-$C_1$-$C_4$-alkylaminocarbonyl, $C_6$-$C_{10}$-arylaminocarbonyl, arylcarbonyl, heteroarylcarbonyl, heterocyclylcarbonyl, heteroaryl, heterocyclyl or cyano, wherein $C_1$-$C_6$-alkylcarbonyl, $C_1$-$C_6$-alkoxycarbonyl, mono- and di-$C_1$-$C_4$-alkylaminocarbonyl can be further substituted with one to three identical or different radicals selected from the group consisting of $C_3$-$C_8$-cycloalkyl, hydroxy, $C_1$-$C_4$-alkoxy, $C_1$-$C_4$-alkoxycarbonyl, hydroxycarbonyl, aminocarbonyl, mono- and di-$C_1$-$C_4$-alkylaminocarbonyl, $C_1$-$C_4$-alkylcarbonylamino, 1-C4-alkylcarbonyl)-$C_1$-$C_4$-alkylamino, cyano, amino, mono- and di-$C_1$-$C_4$-alkylamino, heteroaryl, heterocyclyl and tri-($C_1$-$C_6$-alkyl)-silyl, and wherein heteroarylcarbonyl, heterocyclylcarbonyl, heteroaryl and heterocyclyl can be further substituted with $C_1$-$C_4$-alkyl, $R^5$ represents $C_1$-$C_4$-alkyl, which can be substituted with one to three identical or different radicals selected from the group consisting of halogen, hydroxy, $C_1$-$C_6$-alkoxy, $C_1$-$C_6$-alkenoxy, $C_1$-$C_6$-alkylthio, amino, mono- and di-$C_1$-$C_6$-alkylamino, arylamino, hydroxycarbonyl, $C_1$-$C_6$-alkoxycarbonyl and the radical —O—$C_1$-$C_4$-alkyl-O—$C_1$-$C_4$-alkyl, or $R^5$ represents amino, $R^6$ represents hydrogen, $C_1$-$C_6$-alkyl, formyl, aminocarbonyl, mono- or di-$C_1$-$C_4$-alkylaminocarbonyl, $C_3$-$C_8$-cycloalkylcarbonyl, $C_1$-$C_6$-alkylcarbonyl, $C_1$-$C_6$-alkoxycarbonyl, N—($C_1$-$C_4$-alkylsulfonyl)-aminocarbonyl, N—($C_1$-$C_4$-alkylsulfonyl)-N—($C_1$-$C_4$-alkyl)-aminocarbonyl, heteroaryl, heterocyclyl, heteroarylcarbonyl or heterocyclylcarbonyl, wherein $C_1$-$C_6$-alkyl, mono- and di-$C_1$-$C_4$-alkylaminocarbonyl, $C_1$-$C_6$-alkylcarbonyl, $C_1$-$C_6$-alkoxycarbonyl, heteroaryl and heterocyclyl can be substituted with one to three identical or different radicals selected from the group consisting of aryl, heteroaryl, hydroxy, $C_1$-$C_4$-alkoxy, hydroxycarbonyl, $C_1$-$C_6$-alkoxycarbonyl, aminocarbonyl, mono- and di-$C_1$-$C_4$-alkylaminocarbonyl, amino, mono- and di-$C_1$-$C_4$-alkylamino, $C_1$-$C_4$-alkylcarbonylamino, tri-($C_1$-$C_6$-alkyl)-silyl, cyano, mono- and di-$C_1$-$C_4$-alkylamino-$C_1$-$C_4$-alkylaminocarbonyl, $C_1$-$C_4$-alkoxy-$C_1$-$C_4$-alkylaminocarbonyl and halogen, or $R^6$ represents a moiety of the formula

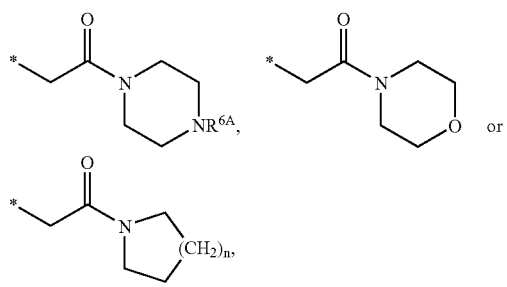

wherein
R$^{6A}$ is selected from the group consisting of hydrogen and C$_1$-C$_6$-alkyl, and n represents an integer of 1 or 2, R$^7$ represents halogen, nitro, cyano, C$_1$-C$_6$-alkyl, hydroxy or C$_1$-C$_6$-alkoxy, wherein C$_1$-C$_6$-alkyl is further substituted with one to three identical or different radicals selected from the group consisting of halogen, hydroxy and C$_1$-C$_4$-alkoxy, and C$_1$-C$_6$-alkoxy can be further substituted with one to three identical or different radicals selected from the group consisting of halogen, hydroxy and C$_1$-C$_4$-alkoxy, and Y$^1$, Y$^2$, Y$^3$, Y$^4$ and Y$^5$ independently from each other represent CH or N, wherein the ring contains either 0, 1 or 2 nitrogen atoms, or a pharmaceutically acceptable salt thereof.

2. The compound of general formula (I) according to claim 1, wherein

A represents an aryl or heteroaryl ring,

R$^1$, R$^2$ and R$^3$ independently from each other represent hydrogen, halogen, nitro, cyano, C$_1$-C$_6$-alkyl, hydroxy or C$_1$-C$_6$-alkoxy, wherein C$_1$-C$_6$-alkyl and C$_1$-C$_6$-alkoxy can be further substituted with one to three identical or different radicals selected from the group consisting of halogen, hydroxy and C$_1$-C$_4$-alkoxy, R$^4$ represents C$_1$-C$_6$-alkylcarbonyl, C$_1$-C$_6$-alkoxycarbonyl, C$_1$-C$_6$-alkenoxycarbonyl, hydroxycarbonyl, aminocarbonyl, mono- or di-C$_1$-C$_4$-alkylaminocarbonyl, C$_6$-C$_{10}$-arylaminocarbonyl, heteroarylcarbonyl, heterocyclylcarbonyl, heteroaryl, heterocyclyl or cyano, wherein C$_1$-C$_6$-alkylcarbonyl, C$_1$-C$_6$-alkoxycarbonyl, mono- and di-C$_1$-C$_4$-alkylaminocarbonyl can be further substituted with one to three identical or different radicals selected from the group consisting of C$_3$-C$_8$-cycloalkyl, hydroxy, C$_1$-C$_4$-alkoxy, C$_1$-C$_4$-alkoxycarbonyl, hydroxycarbonyl, aminocarbonyl, mono- and di-C$_1$-C$_4$-alkylaminocarbonyl, C$_1$-C$_4$-alkylcarbonylamino, amino, mono- and di-C$_1$-C$_4$-alkylamino, heteroaryl, heterocyclyl and tri-(C$_1$-C$_6$-alkyl)-silyl, R$^5$ represents C$_1$-C$_4$-alkyl, which can be substituted with one to three identical or different radicals selected from the group consisting of halogen, hydroxy, C$_1$-C$_6$-alkoxy, C$_1$-C$_6$-alkenoxy, C$_1$-C$_6$-alkylthio, amino, mono- and di-C$_1$-C$_6$-alkylamino, arylamino, hydroxycarbonyl, C$_1$-C$_6$-alkoxycarbonyl and the radical —O—C$_1$-C$_4$-alkyl-O—C$_1$-C$_4$-alkyl, or R$^5$ represents amino, R$^6$ represents hydrogen, C$_1$-C$_6$-alkyl, formyl, aminocarbonyl, mono- or di-C$_1$-C$_4$-alkylaminocarbonyl, C$_3$-C$_8$-cycloalkylcarbonyl, C$_1$-C$_6$-alkylcarbonyl, C$_1$-C$_6$-alkoxycarbonyl, N—(C$_1$-C$_4$-alkylsulfonyl)-aminocarbonyl, N—(C$_1$-C$_4$-alkylsulfonyl)-N—(C$_1$-C$_4$-alkyl)-aminocarbonyl, heteroaryl, heterocyclyl, heteroarylcarbonyl or heterocyclylcarbonyl, wherein C$_1$-C$_6$-alkyl, mono- and di-C$_1$-C$_4$-alkylaminocarbonyl, C$_1$-C$_6$-alkylcarbonyl, C$_1$-C$_6$-alkoxycarbonyl, heteroaryl and heterocyclyl can be substituted with one to three identical or different radicals selected from the group consisting of aryl, heteroaryl, hydroxy, C$_1$-C$_4$-alkoxy, hydroxycarbonyl, C$_1$-C$_6$-alkoxycarbonyl, aminocarbonyl, mono- and di-C$_1$-C$_4$-alkylaminocarbonyl, amino, mono- and di-C$_1$-C$_4$-alkylamino, C$_1$-C$_4$-alkylcarbonylamino, tri-(C$_1$-C$_6$-alkyl)-silyl, cyano, mono- and di-C$_1$-C$_4$-alkylamino-C$_1$-C$_4$-alkylaminocarbonyl, C$_1$-C$_4$-alkoxy-C$_1$-C$_4$-alkylaminocarbonyl and halogen, or R$^6$ represents a moiety of the formula

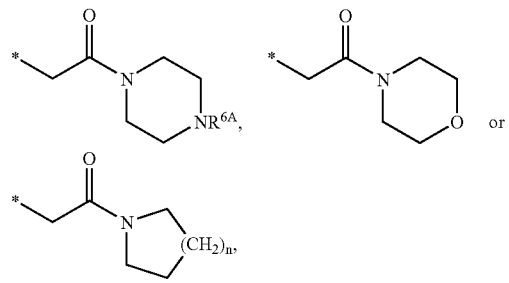

wherein

R$^{6A}$ is selected from the group consisting of hydrogen and C$_1$-C$_6$-alkyl, and n represents an integer of 1 or 2, R$^7$ represents halogen, nitro, cyano, C$_1$-C$_6$-alkyl, hydroxy or C$_1$-C$_6$-alkoxy, wherein C$_1$-C$_6$-alkyl is further substituted with one to three identical or different radicals selected from the group consisting of halogen, hydroxy and C$_1$-C$_4$-alkoxy, and C$_1$-C$_6$-alkoxy can be further substituted with one to three identical or different radicals selected from the group consisting of halogen, hydroxy and C$_1$-C$_4$-alkoxy, and Y$^1$, Y$^2$, Y$^3$, Y$^4$ and Y$^5$ independently from each other represent CH or N, wherein the ring contains either 0, 1 or 2 nitrogen atoms.

3. The compound of general formula (I) according to claim 1, wherein

A represents a phenyl, naphthyl or pyridyl ring,

R$^1$, R$^2$ and R$^3$ independently from each other represent hydrogen, fluoro, chloro, bromo, nitro, cyano, methyl, ethyl, trifluoromethyl or trifluoromethoxy, R$^4$ represents C$_1$-C$_6$-alkylcarbonyl, C$_1$-C$_6$-alkoxycarbonyl, hydroxycarbonyl, aminocarbonyl, mono-C$_1$-C$_4$-alkylaminocarbonyl or cyano, wherein C$_1$-C$_6$-alkylcarbonyl, C$_1$-C$_6$-alkoxycarbonyl and mono-C$_1$-C$_4$-alkylaminocarbonyl can be substituted with one to three identical or different radicals selected from the group consisting of C$_3$-C$_8$-cycloalkyl, hydroxy, C$_1$-C$_4$-alkoxy, C$_1$-C$_4$-alkoxycarbonyl, amino, mono- or di-C$_1$-C$_4$-alkylamino, heteroaryl and heterocyclyl, R$^5$ represents methyl or ethyl, R$^6$ represents hydrogen, C$_1$-C$_6$-alkyl, mono- or di-C$_1$-C$_4$-alkylaminocarbonyl, C$_1$-C$_6$-alkylcarbonyl, C$_1$-C$_6$-alkoxycarbonyl or heterocyclylcarbonyl, wherein C$_1$-C$_6$-alkyl and C$_1$-C$_6$-alkoxycarbonyl can be substituted with one to three identical or different radicals selected from the group consisting of heteroaryl, hydroxy, C$_1$-C$_4$-alkoxy, hydroxycarbonyl, C$_1$-C$_6$-alkoxycarbonyl, aminocarbonyl, mono- and di-C$_1$-C$_4$-alkylaminocarbonyl, cyano, amino, mono- and di-C$_1$-C$_4$-alkylamino, or R⁶ represents a moiety of the formula

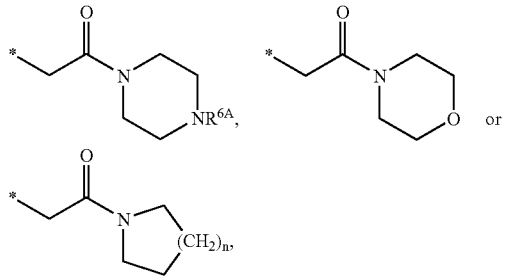

wherein
R⁶ᴬ is selected from the group consisting of hydrogen and $C_1$-$C_4$-alkyl, and
n represents an integer of 1 or 2,
R⁷ represents halogen, nitro, cyano, trifluoromethyl, or trifluoromethoxy,
and
$Y^1, Y^2, Y^3, Y^4$ and $Y^5$ each represent CH.

4. The compound of general formula (I) according to claim 1, wherein
A represents a phenyl or a pyridyl ring,
R¹ and R³ each represent hydrogen,
R² represents fluoro, chloro, bromo, nitro or cyano,
R⁴ represents cyano, $C_1$-$C_4$-alkylcarbonyl or $C_1$-$C_4$-alkoxycarbonyl, wherein $C_1$-$C_4$-alkoxycarbonyl can be substituted with a radical selected from the group consisting of hydroxy, $C_1$-$C_4$-alkoxy, $C_1$-$C_4$-alkoxycarbonyl, mono- and di-$C_1$-$C_4$-alkylamino, heteroaryl and heterocyclyl,
R⁵ represents methyl,
R⁶ represents hydrogen, $C_1$-$C_4$-alkyl, mono- or di-$C_1$-$C_4$-alkylaminocarbonyl, $C_1$-$C_4$-alkylcarbonyl or $C_1$-$C_4$-alkoxycarbonyl, wherein $C_1$-$C_4$-alkyl and $C_1$-$C_4$-alkoxycarbonyl can be substituted with a radical selected from the group consisting of heteroaryl, hydroxy, $C_1$-$C_4$-alkoxy, hydroxycarbonyl, aminocarbonyl, mono- and di-$C_1$-$C_4$-alkylaminocarbonyl, amino, mono- and di-$C_1$-$C_4$-alkylamino,
or
R⁶ represents a moiety of the formula

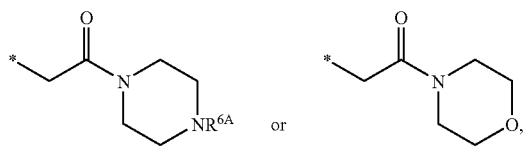

wherein
R⁶ᴬ is selected from the group consisting of hydrogen and methyl,
R⁷ represents trifluoromethyl or nitro,
and
$Y^1, Y^2, Y^3, Y^4$ and $Y^5$ each represent CH.

5. The compound of general formula (I) according to claim 1, wherein A is phenyl or pyridyl.
6. The compound of general formula (I) according to claim 1, wherein R¹ is hydrogen.
7. The compound of general formula (I) according to claim 1, wherein R² is cyano.
8. The compound of general formula (I) according to claim 1, wherein R³ is hydrogen.
9. The compound of general formula (I) according to claim 1, wherein R⁴ is $C_1$-$C_4$-alkoxycarbonyl optionally substituted by hydroxy or wherein R⁴ is $C_1$-$C_4$-alkylcarbonyl.
10. The compound of general formula (I) according to claim 1, wherein R⁵ methyl.
11. The compound of general formula (I) according to claim 1, wherein R⁶ is hydrogen.
12. The compound of general formula (I) according to claim 1, wherein R⁷ is trifluoromethyl or nitro.
13. A compound of general formula (IA)

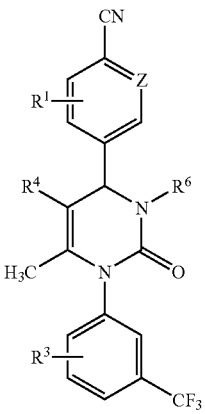

wherein
Z represents CH or N, and
R¹, R³, R⁴ and R⁶ have the meaning indicated in claim 1.

14. A process for synthesizing the compounds of general formula (I), as defined in claim 1 by condensing compounds of general formula (II)

(II)

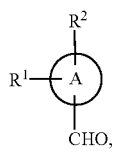

wherein
A, R¹ and R² the meaning indicated in claim 1,
with compounds of general formula (III)

(III)

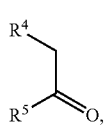

wherein
R⁴ and R⁵ have the meaning indicated in claim 1,
and compounds of general formula (IV)

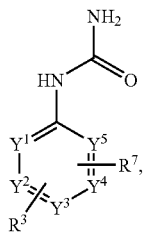
(IV)

wherein
R³, R⁷, and Y¹ to Y⁵ have the meaning indicated in claim 1,
in the presence of an acid either in a three-component/one-step reaction or sequentially to give compounds of the general formula (IB)

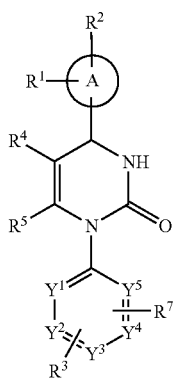

wherein
A, R¹ to R⁵, R⁷, and Y¹ to Y⁵ have the meaning indicated in claim 1, optionally followed by reaction of the compounds of general formula (IB) with compounds of the general formula (V)

R⁶*—X   (V), wherein
R⁶* has the meaning of R⁶ as indicated in claim 1, but does not represent hydrogen, and
X represents a leaving group,
in the presence of a base.

15. A composition containing at least one compound of general formula (I) as defined in claim 1 and a pharmacologically acceptable diluent.

16. A process for preparation of a composition, said process comprising a step of bringing the compounds of general formula (I) as defined in claim 1 together with customary auxiliaries into a suitable application form; wherein said composition contains at least one compound of general formula (I) and a pharmacologically acceptable diluent.

17. A method of treating chronic obstructive pulmonary disease or acute myocardial infarction, said method comprising administering a therapeutically effective amount of a compound of claim 1.

18. The method of claim 17, wherein a neutrophil elastase inhibitory amount is administered.

19. A composition containing at least one compound of general formula (IA) as defined in claim 13 and a pharmacologically acceptable diluent.

20. A process for preparation of a composition, said process comprising a step of bringing the compounds of general formula (IA) as defined in claim 13 together with customary auxiliaries into a suitable application form; wherein said composition contains at least one compound of general formula (IA) and a pharmacologically acceptable diluent.

21. Ethyl 4-(4-cyanophenyl)-6-methyl-1-(3-methylphenyl)-2-oxo-1,2,3,4-tetrahydro-5-pyrimidinecarboxylate, or a pharmaceutically acceptable salt thereof.

22. A compound according to claim 1, having the following structure:

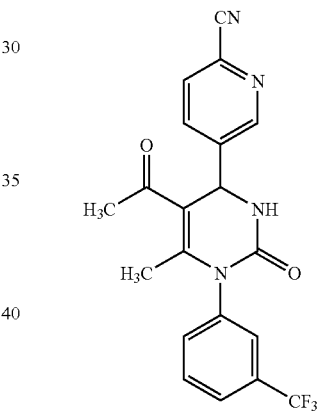

(5-{5-Acetyl-6-methyl-2-oxo-1-[3-(trifluoromethyl)phenyl]-1,2,3,4-tetrahydro-4- pyrimidinyl}-2-pyridinecarbonitrile)
or a pharmaceutically acceptable salt thereof.

23. A compound according to claim 22, having the formula (+)-5-{5-Acetyl-6- methyl-2-oxo-1-[3-(trifluoromethyl)phenyl]-1,2,3,4-tetrahydro-4-pyrimidinyl}-2- pyridinecarbonitrile, or a pharmaceutically acceptable salt thereof.

* * * * *